(12) United States Patent
Chang et al.

(10) Patent No.: US 9,254,485 B2
(45) Date of Patent: Feb. 9, 2016

(54) SYSTEMS AND METHODS FOR AN INTEGRATED BIO-ENTITY MANIPULATION AND PROCESSING DEVICE

(71) Applicant: Taiwan Semiconductor Manufacturing Company, Ltd., Hsin-Chu (TW)

(72) Inventors: Yi-Hsien Chang, Changhua County (TW); Chu-Ren Cheng, Hsin-Chu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 14/621,987

(22) Filed: Feb. 13, 2015

(65) Prior Publication Data

US 2015/0174574 A1    Jun. 25, 2015

Related U.S. Application Data

(63) Continuation-in-part of application No. 13/716,709, filed on Dec. 17, 2012.

(51) Int. Cl.
*G01N 27/447* (2006.01)
*B01L 3/00* (2006.01)
(Continued)

(52) U.S. Cl.
CPC ..... *B01L 3/502715* (2013.01); *B01L 3/502792* (2013.01); *B81B 1/00* (2013.01); *G01N 27/44791* (2013.01); *G01N 33/54366* (2013.01); *B01L 2300/0654* (2013.01); *B01L 2300/0816* (2013.01); *B01L 2300/0887* (2013.01); *B01L 2300/161* (2013.01); *B01L 2400/043* (2013.01); *B01L 2400/0424* (2013.01); *B01L 2400/0427* (2013.01)

(58) Field of Classification Search
CPC .......... B01L 3/50784; B01L 3/502792; B01L 2400/0427
See application file for complete search history.

(56) References Cited

U.S. PATENT DOCUMENTS 6,620,625 B2    9/2003  Wolk et al.
7,189,359 B2 *  3/2007  Yuan et al. ................. 422/82.01
(Continued)

FOREIGN PATENT DOCUMENTS

TW    201244824       11/2012
TW    201244824 A1    11/2012

OTHER PUBLICATIONS

Lin Luan et al., Integrated Optical Sensor in a Digital Microfluidic Platform, IEEE Sensors Journal, vol. 8, No. 5, May 2008.
(Continued)

*Primary Examiner* — Alexander Noguerola
(74) *Attorney, Agent, or Firm* — Haynes and Boone, LLP

(57) ABSTRACT

An integrated semiconductor device for manipulating and processing bio-entity samples is disclosed. The device includes a microfluidic channel formed between a first substrate and a second substrate and a microfluidic grid formed over the first substrate and coupled to the microfluidic channel to manipulate a droplet within the microfluidic channel. The device further includes a magnetic field generation device included in the microfluidic grid and fluidic control circuitry coupled to the magnetic device to facilitate control of the magnetic field generation device to manipulate the droplet, when the droplet contains at least one magnetic bead, within the microfluidic channel.

20 Claims, 16 Drawing Sheets

(51) Int. Cl.
*B81B 1/00* (2006.01)
*G01N 33/543* (2006.01)

(56) References Cited

U.S. PATENT DOCUMENTS

| | | | | |
|---|---|---|---|---|
| 8,367,370 | B2* | 2/2013 | Wheeler et al. | 435/29 |
| 2004/0231990 | A1 | 11/2004 | Aubry et al. | |
| 2008/0053205 | A1* | 3/2008 | Pollack et al. | 73/61.71 |
| 2010/0200781 | A1 | 8/2010 | Khorasani et al. | |
| 2010/0236928 | A1* | 9/2010 | Srinivasan et al. | 204/450 |
| 2010/0279374 | A1* | 11/2010 | Sista et al. | 435/173.9 |
| 2011/0118132 | A1* | 5/2011 | Winger et al. | 506/7 |
| 2013/0293878 | A1 | 11/2013 | Chang et al. | |
| 2014/0166484 | A1 | 6/2014 | Chang et al. | |
| 2014/0262783 | A1 | 9/2014 | Chang et al. | |
| 2014/0299472 | A1 | 10/2014 | Chang et al. | |

OTHER PUBLICATIONS

Korean Search Report dated Dec. 17, 2012 cited in Taiwanese Office Action, not translated.

Lin Luan, Randall D. Evans, Nan M. Jokerst, and Richard B. Fair, Integrated Optical Sensor in a Digital Microfluidic Platform, May 2008, pp. 628-635, vol. 8, No. 5, IEEE Sensors Journal.

U.S. Appl. No. 13/716,709, filed Dec. 17, 2012, by inventors Yiu-Hsien Chang and Chun-Ren Cheng for "Systems and Methods for an Integrated Bio-Entity Manipulation and Processing Semiconductor Device," 23 pages of text, 9 pages of drawings.

U.S. Appl. No. 14/200,148, filed Mar. 7, 2014, by inventors Kuo-Cheng Ching, Chih-Hao Wang, Zhiqiang Wu, Carlos H. Diaz, and Jean-Pierre Colinge for "Semiconductor Arrangement and Formation Thereof," 17 pages of text, 7 pages of drawings.

Mark A Burns et al., "An Integrated Nanoliter DNA Analysis Device," Science, published by American Association for the Advancement of Science, Oct. 16, 1998, vol. 282, pp. 484-487.

Aaron R. Wheeler, "Putting Electrowetting to Work," Science, published by American Association for the Advancement of Science, Oct. 24, 2008, vol. 322, pp. 539-540.

Mohamed Abdelgawad et al., "The Digital Revolution: A New Paradigm for Microfluidics," 2009 Wiley-VCH Verlag GmbH & Co. KGaA Weinheim, pp. 920-925.

* cited by examiner

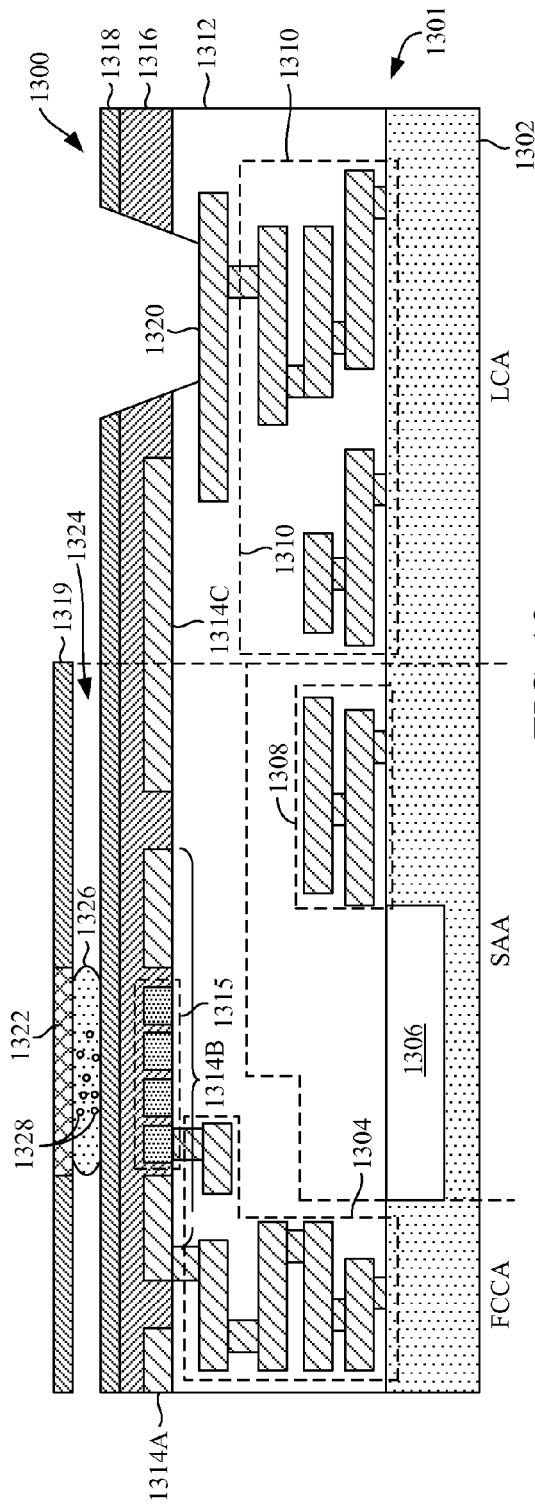
FIG. 13
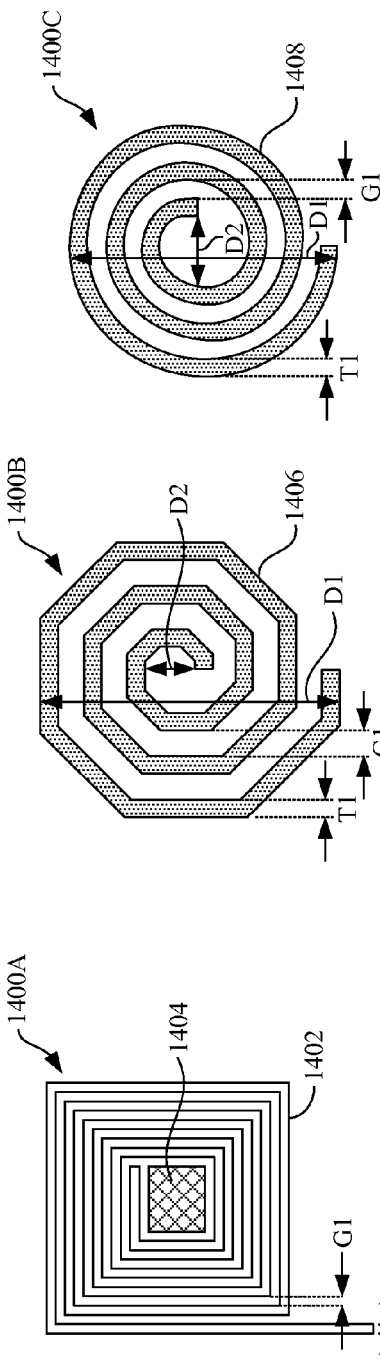
FIG. 14A
FIG. 14B
FIG. 14C

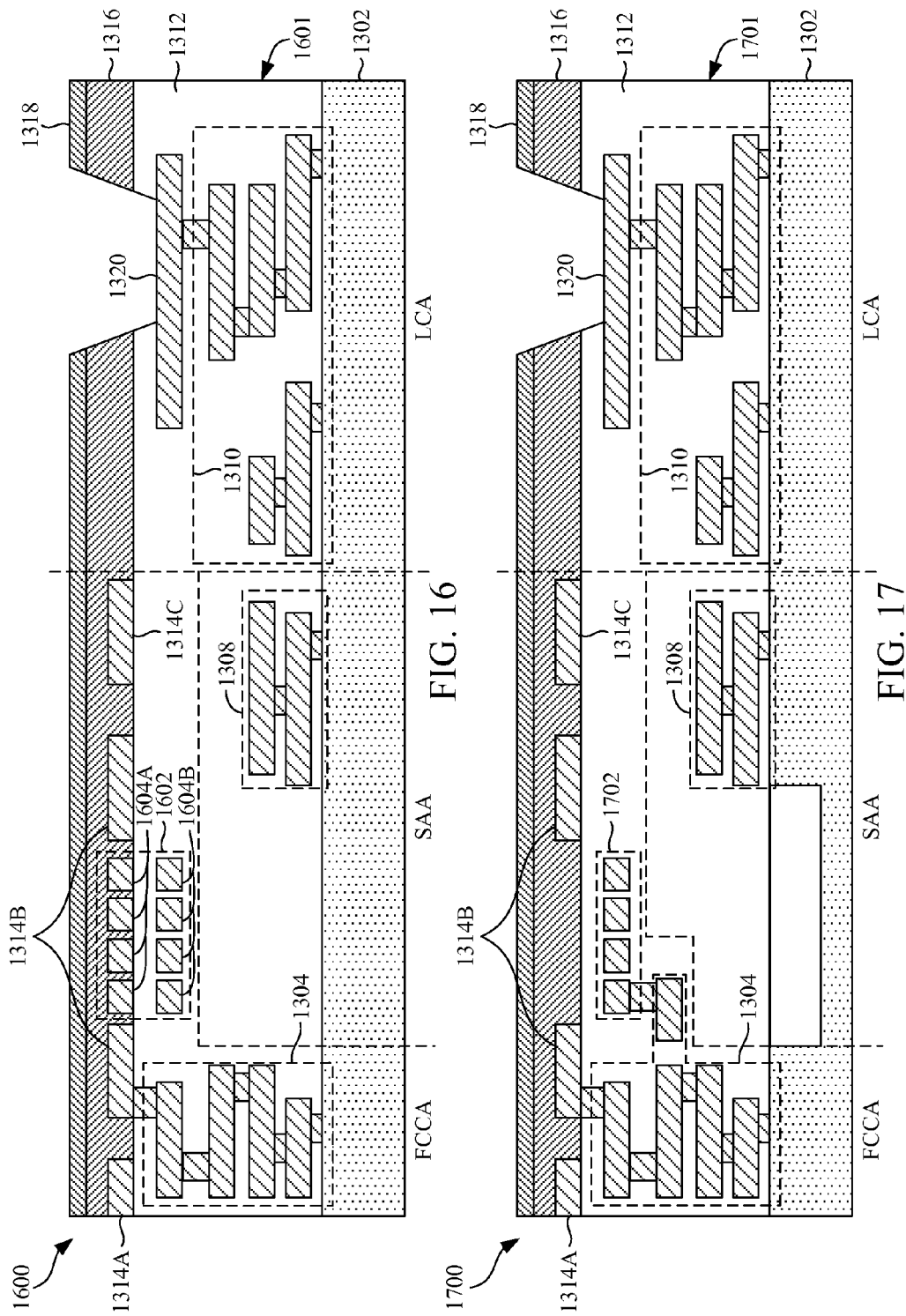

SYSTEMS AND METHODS FOR AN INTEGRATED BIO-ENTITY MANIPULATION AND PROCESSING DEVICE

PRIORITY CLAIM AND CROSS-REFERENCE

This is a continuation-in-part of U.S. Ser. No. 13/716,709 filed on Dec. 17, 2012, the entire disclosure of which is hereby incorporated by reference.

The present disclosure is related to the following commonly-assigned patent applications, the entire disclosures of which are incorporated herein by reference: U.S. patent application Ser. No. 13/830,234 filed on Mar. 14, 2013 now U.S. Publication No. 2014/0262783, entitled "OPTICAL DETECTION FOR BIO-ENTITIES", U.S. patent application Ser. No. 14/200,148 filed on Mar. 7, 2014, entitled "SEMICONDUCTOR ARRANGEMENT AND FORMATION THEREOF", and U.S. patent application Ser. No. 14/310,440 filed on Jun. 20, 2014 now U.S. Publication No. 2014/0299472, entitled "SYSTEMS AND METHODS FOR AN INTEGRATED BIO-ENTITY MANIPULATION AND PROCESSING SEMICONDUCTOR DEVICE".

BACKGROUND

Medical technology industries, including device manufacturers as well as pharmaceuticals and biologics manufacturers, have experienced significant commercial and technological growth over the past several decades. For example, since the discovery of DNA, our understanding of its bio-informational role in the development, operation, and interaction of pathogens and all living beings has significantly increased thanks to the development of DNA sequencing techniques over the years. Through improvement in DNA sequencing detection techniques, scientists and doctors have gained greater insight on diseases as well as more effective treatments for patients based on their genetic dispositions. Thus, the use and role of DNA sequencing results in health care has increased significantly.

DNA sequences are series of the nucleotide bases adenine, guanine, cytosine, and thymine, that dictate the formation of proteins in biological systems. By analyzing a DNA sequence, important information can be gleaned for both diagnostic and therapeutic purposes. Additionally, the identification and quantification of other biological entities (bio-entities), such as proteins, small molecules, antibodies, and pathogens has pushed forward the potential of medical knowledge to benefit humankind.

There is currently a wide variety of bio-entity manipulation and processing techniques in use today that include the use of amplification and labeling techniques within various methods that may allow for optical detection. This may be done by using fluorescent dyes and external optical systems with analog-to-digital conversion systems to allow for the intensive computer processing required for handling the large amounts of data produced. However, many technical obstacles still exist, such as controlling the fluid samples containing the bio-entity to be observed. Additionally, while the price of DNA sequencing has fallen considerably since the Human Genome Project was completed, further cost savings are needed before the full power of DNA sequencing can have an impact. Therefore, current bio-entity manipulation and processing technologies have not been completely satisfactory.

BRIEF DESCRIPTION OF THE DRAWINGS

Aspects of the present disclosure are best understood from the following detailed description when read with the accompanying figures. It is emphasized that, in accordance with the standard practice in the industry, various features of the figures are not drawn to scale. In fact, the dimensions of the various features may be arbitrarily increased or decreased for clarity of discussion.

FIG. 13 is a cross-sectional diagram of a microfluidic bio-entity manipulation and processing system according to some additional embodiments that includes a magnetic field generation device.

FIGS. 14A, 14B, and 14C are top view diagrams of magnetic field generation devices according to some embodiments.

FIG. 16 is a cross-sectional diagram of a lower substrate of a microfluidic bio-entity manipulation and processing system according to some embodiments that include a magnetic field generation device.

FIG. 17 is a cross-sectional diagram of a lower substrate of a microfluidic bio-entity manipulation and processing system according to an embodiment that include a magnetic field generation device.

DETAILED DESCRIPTION

It is to be understood that the following disclosure provides many different embodiments and examples for implementing different features and aspects of bio-entity detection and identification systems. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features in the figures may be arbitrarily drawn in different scales for the sake of simplicity and clarity. Where features depicted in the various figures are common between two or more figures, the same identifying numerals have been used for clarity of description. However, this should not be understood as limiting such features.

Figure 1:
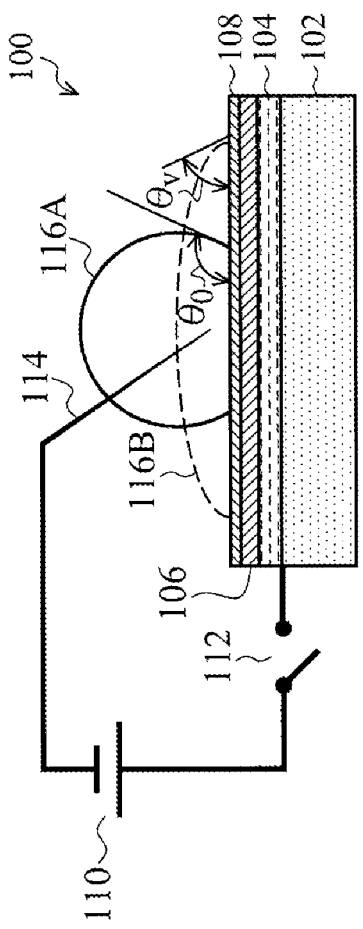
FIG. 1 is a cross-sectional diagram of an electrowetting-on-dielectric apparatus.

FIG. 1 is a cross-sectional diagram of an electro-wetting-on-dielectric (EWOD) apparatus 100. The apparatus 100 includes a substrate 102 with three material layers thereon. These material layers include an electrode layer 104, a dielectric layer 106, and a hydrophobic coating 108. The electrode layer 104 is coupled to a variable voltage source 110 by a switch 112. Attached to the opposite end of the voltage source 110 is a probe 114. As depicted in FIG. 1, the apparatus 100 positions the probe 114 to be inserted into a droplet shown in two different states. Droplet 116A depicts the droplet in a state when no voltage is being applied by probe 114. Because of the hydrophobic coating 108, droplet 116A has a contact angle $\theta_0$ as shown. By applying a voltage from the voltage source 110 through the probe 114, the contact angle can be decreased and the contact area increased. Thus, droplet 116B is the droplet when a voltage is applied. The contact angle is then decreased to $\theta_V$, bringing the mass of the droplet 116B closer to the underlying electrode layer 104. The change in the contact angle caused by the applied voltage is related to the applied voltage according to equation (1) below.

$$\cos\theta_V - \cos\theta_0 = \frac{\varepsilon\varepsilon_o}{2\gamma_{LG}t}V^2 \quad (1)$$

In equation (1), V is the applied electrical potential or voltage, $\theta_V$ is the contact angle under applied voltage V, and $\theta_0$ is the contact angle without applied voltage V. Other variables include: $\varepsilon$, the dielectric constant of the dielectric layer 106; $\varepsilon_0$, the vacuum permittivity; $\gamma_{LG}$, the surface tension; and t, the thickness of dielectric layer 106. This manipulation of the apparent hydrophobicity of the droplet in apparatus 100 may be referred to as electrowetting-on-dielectric (EWOD). Thus, by using EWOD, the physical configuration and behavior of a droplet on a hydrophobic surface can be altered and controlled as seen in FIG. 1

Figure 2:
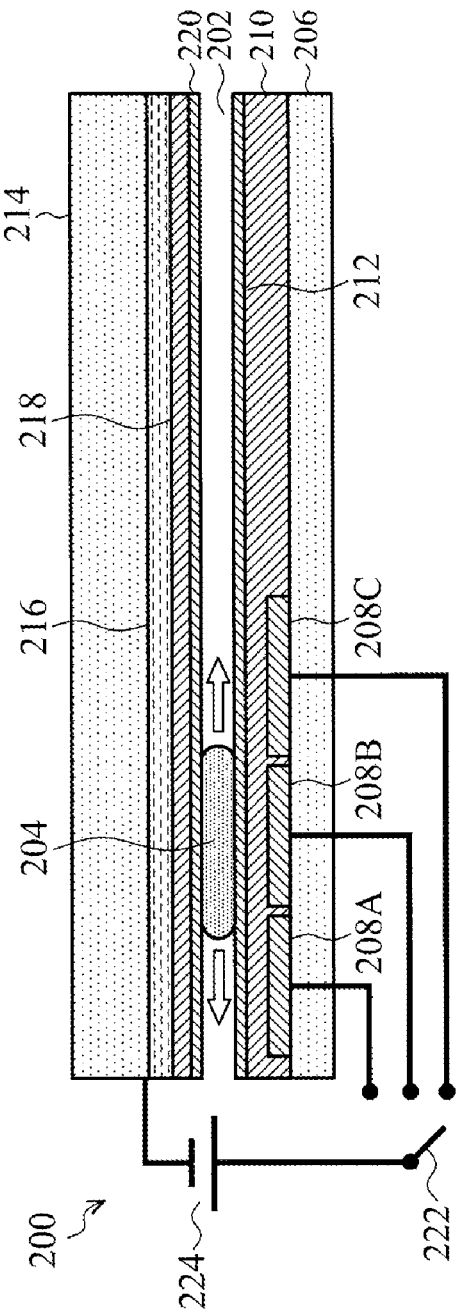
FIG. 2 is a cross-sectional diagram of a fluidic control system that uses electrowetting to transport and manipulate bio-entity sample droplets.

FIG. 2 is a cross-sectional diagram of a fluidic control system 200 that allows for transporting and manipulating bio-entity sample droplets using EWOD principles. The fluidic control system 200 operates around a microfluidic channel 202 to control a droplet 204 within the channel. Droplet 204 is a bio-entity sample droplet. A "bio-entity" or "biological entity" as used herein may refer to DNA, RNA, a protein, a small molecule, a virus or other pathogen, or any such thing that may be sequenced, identified, or quantified. Such activities may take place in a medical or industrial context. Throughout the disclosure, the example of DNA sequencing is presented, however the embodiments are not limited to this example.

As seen in FIG. 2, the bottom portion of the microfluidic channel 202 is provided by a first substrate 206 with several layers thereon. These layers include three electrodes 208A, 208B, and 208C, which are surrounded by a first dielectric layer 210. Above the dielectric layer 210 is a first hydrophobic coating 212 that provides the lower surface of the microfluidic channel 202.

The top surface of the microfluidic channel 202 is provided by another hydrophobic coating, which is formed over a second substrate 214. This second substrate 214 may be a glass substrate, a silicon substrate, or a quartz substrate, etc., upon which several material layers are deposited. These layers include a top electrode layer 216, a second dielectric layer 218, and a second hydrophobic coating 220, which forms the top surface of the microfluidic channel 202. In some embodiments, the channel 202 may be filled with a fluid medium, such as air or silicon oil, for example. The second substrate 214 is inverted and brought close to the surface of the first hydrophobic coating 212. Thus, the droplet 204 is physically bounded by the first hydrophobic coating 212 on the bottom and the second hydrophobic coating 220 on the top.

The bottom electrodes 208A, 208B, and 208C are coupled to a switch 222 capable of selecting any combination of these three electrodes. The switch 222, in turn is connected to a voltage source 224, the opposite side of which is connected to the top electrode layer 216. By selectively applying a voltage to various combinations of electrodes 208A, 208B, and 208C, the electric field in which the droplet 204 is located can be altered. In the depicted embodiment a DC potential is applied, but in other embodiments, an AC potential may be used instead. By controlling the electric fields between the bottom electrodes 208A, 208B, and 208C and the top electrode 216, the droplet 204 itself can be manipulated and transported in various ways. This can be better understood by reference to FIG. 3.

Figure 3:
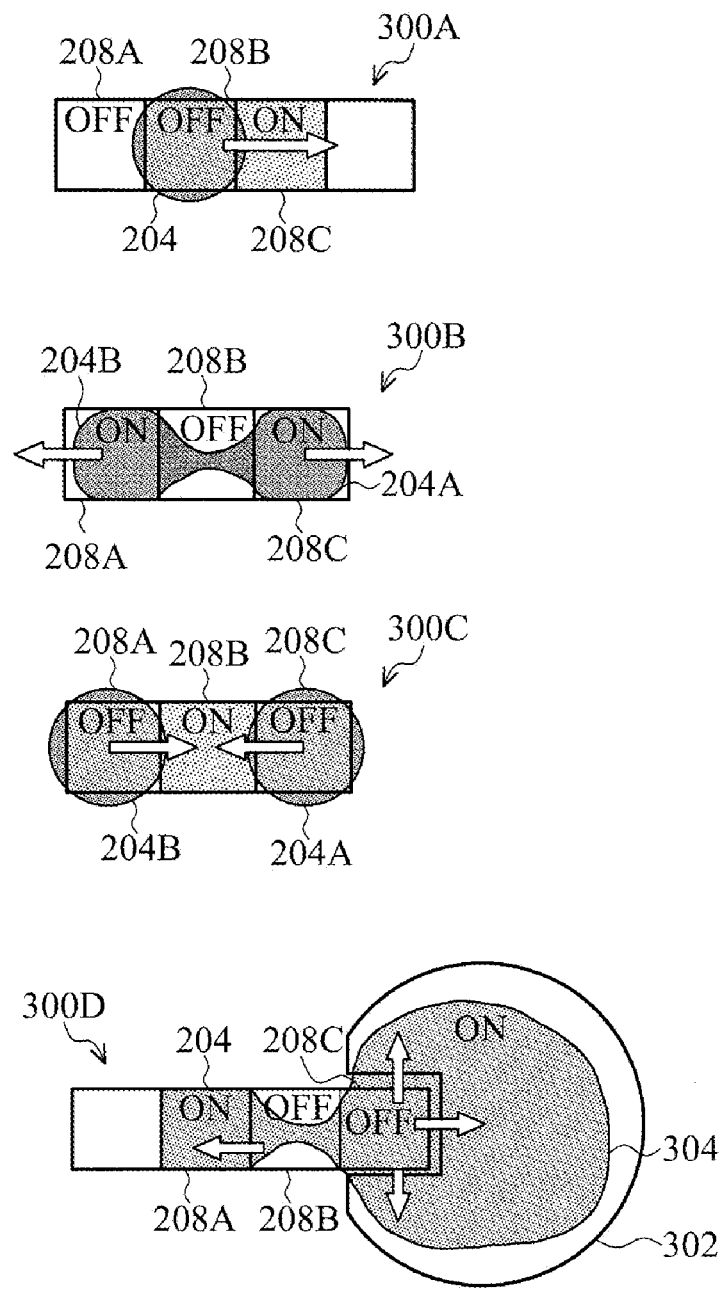
FIG. 3 is a diagram illustrating how certain actions may be achieved using an electrowetting fluidic control system.

FIG. 3 is a diagram illustrating how certain actions may be achieved using an EWOD fluidic control system. Four exemplary actions are depicted: a lateral movement 300A, a droplet split 300B, a droplet merger 300C, and a droplet formation 300D. These examples depict actions performed in the fluidic control system 200 as seen from above, looking down onto the droplet 204 through substrate 214.

As depicted in the lateral movement 300A, the droplet 204 is situated above the electrode 208B. When switch 222 is asserted so that bottom electrode 208A is disconnected from the voltage source 224 (OFF), bottom electrode 208B is OFF, and bottom electrode 208C is connected to the voltage source 224 (ON), the droplet moves in the direction of electrode 208C until it is located over electrode 208C.

As depicted in the droplet split 300B, droplet 204 begins situated above bottom electrode 208B. When switch 222 is asserted so that the bottom electrode 208B is OFF and both bottom electrodes 208A and 208C are ON, the portion of the droplet 204 that is closest to bottom electrode 208A will move to the left and the portion of the droplet 204 that is closest to bottom electrode 208C will move to the right, causing the droplet 204 to be split into a droplet 204A situated over the bottom electrode 208C and a droplet 204B situated over the bottom electrode 208A.

As depicted in the droplet merger 300C, the droplet 204A begins situated above 208C and the droplet 204B begins situated over 208A. When the switch 222 is asserted so that bottom electrodes 208A and 208C are OFF and the bottom electrode 208B is ON, the droplets 204A and 204B both move toward the bottom electrode 208B. The droplets 204A and 204B will merge over the bottom electrode 208B to form a single droplet.

A droplet formation 300D is also depicted in FIG. 3. Droplet formation 300D depicts the formation of a bio-entity sample droplet from a larger bio-entity sample drop. The performance of droplet formation 300D uses the three bottom electrodes 208A, 208B, and 208C, as discussed, and further includes a larger electrode 302. The larger electrode 302 may allow for the placement of a larger volume of liquid in a drop 304. In order to form a droplet 204, all four electrodes (302, 208A, 208B, and 208C) are turned ON to pull the drop 304 out along the path indicated by the square bottom electrodes, then bottom electrodes 208B and 208C are turned OFF. The liquid over bottom electrodes 208B and 208C is pulled away by the ON state of the other electrodes, and pushed away by the hydrophobicity of the bottom electrodes 208B and 208C in their OFF state. The portion of drop 304 above 208A remains to form droplet 204.

These examples assume that any other adjacent electrodes are OFF. The lateral movement 300A, the droplet split 300B, the droplet merger 300C, and the droplet formation 300D actions may be used to manipulate and transport droplets as they move through the microfluidic channel 202 of FIG. 2, and also through a microfluidic grid.

Figure 4:
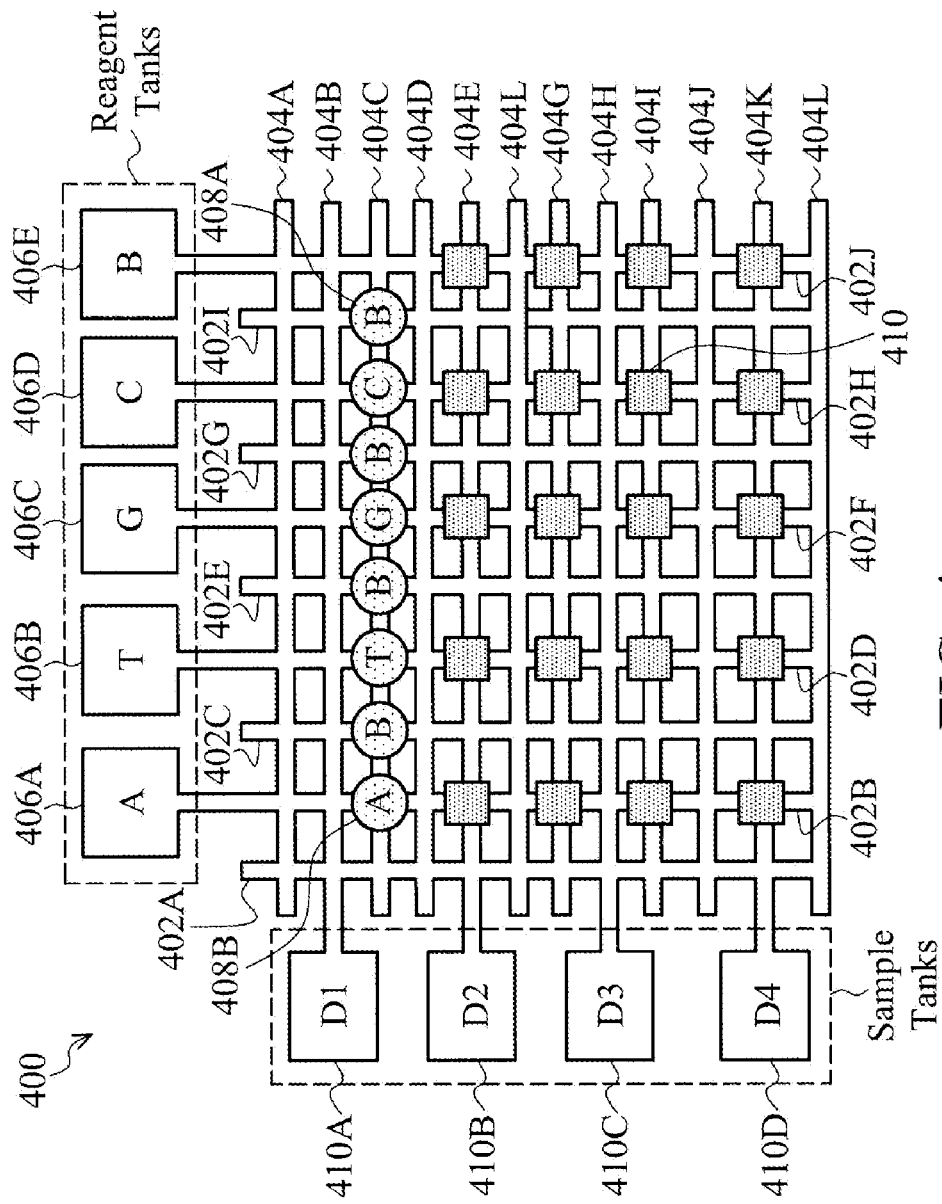
FIG. 4 is a diagram of a microfluidic grid for transporting and mixing target bio-entity samples and biological reagents.

FIG. 4 is a diagram of a microfluidic grid 400 for transporting and mixing target bio-entities. For example, microfluidic grid 400 may be used for transporting and mixing target DNA samples and biological reagents. The microfluidic grid includes a plurality of horizontal and vertical paths lined by electrodes like the electrodes 208A, 208B, and 208C of FIG. 2. Actions like those described in connection with FIG. 3 may be used to move, split, merge, and form droplets in the microfluidic grid 400.

The plurality of vertical paths is labeled as vertical paths 402A-J, while the plurality of horizontal paths is labeled as horizontal paths 404A-L. Each of vertical paths 402A-J and each of horizontal paths 404A-L may be formed from a plurality of linearly arranged electrodes. The spaces in between the vertical paths 402A-J and the horizontal paths 404A-L may be empty space as the hydrophobic coatings 212 and 220 may effectively bar a droplet from "jumping" from one hydrophilic path to another with electrodes in an ON state. In some embodiments, material barriers exist in the spaces between the paths.

The microfluidic grid 400 also includes a plurality of tanks from which droplets are introduced into the plurality of paths. Arranged along the top is a number of reagent tanks 406A-E. In the depicted embodiment of microfluidic grid 400, these reagent tanks include an adenine reagent tank 406A, a thymine reagent tank 406B, a guanine reagent tank 406C, a cytosine reagent tank 406D, and a buffer tank 406E. Other embodiments of microfluidic grid 400 may include other biological reagents. Droplets may be dispensed into the microfluidic grid 400 through vertical paths 402B, 402D, 402F, 402H, and 402J, and by selectively asserting the electrodes that make up the horizontal and vertical paths, these droplets may be positioned anywhere in the microfluidic grid 400 and divided and mixed, or merged, with other droplets. A number of reagent droplets, including exemplary buffer droplet 408A and exemplary adenine reagent droplet 408B, are depicted along horizontal path 404C.

Depicted on the left-hand side of microfluidic grid 400 is a number of bio-entity reservoirs or sample tanks 410A-D. In the depicted embodiment, used for DNA sequences, each bio-entity sample tank contains a different target DNA fragment, labeled as D1 in target DNA fragment tank 410A, D2 in target DNA fragment tank 410B, D3 in target DNA fragment tank 410C, and D4 in target DNA fragment tank 410D. In embodiments used for DNA sequencing these tanks hold fragments of a DNA sample to be sequenced. In embodiments used for diagnosis, other types of bio-entity samples, such as antibodies, may be present in the sample tanks.

Sequencing the entire genome of a person or pathogen in a single sequence would require a prohibitively long amount of time. By fragmenting a DNA sample into many samples, each sample may be processed simultaneously in order to decrease the total time required to obtain the entire sequence. The fragments should be labeled beforehand so that the individual parallel sequencing can be recombined. Each square in FIG. 4 is a target DNA fragment, such as exemplary target DNA fragment 410, that can be manipulated as described above in connection with FIG. 3, including being mixed with a reagent droplet for tagging. The area underneath the microfluidic grid 400 includes a light sensor array, which may be used to take light-based measurements in order to sequence the target DNA fragment samples. This may be better understood with reference to FIG. 5.

Figure 5:
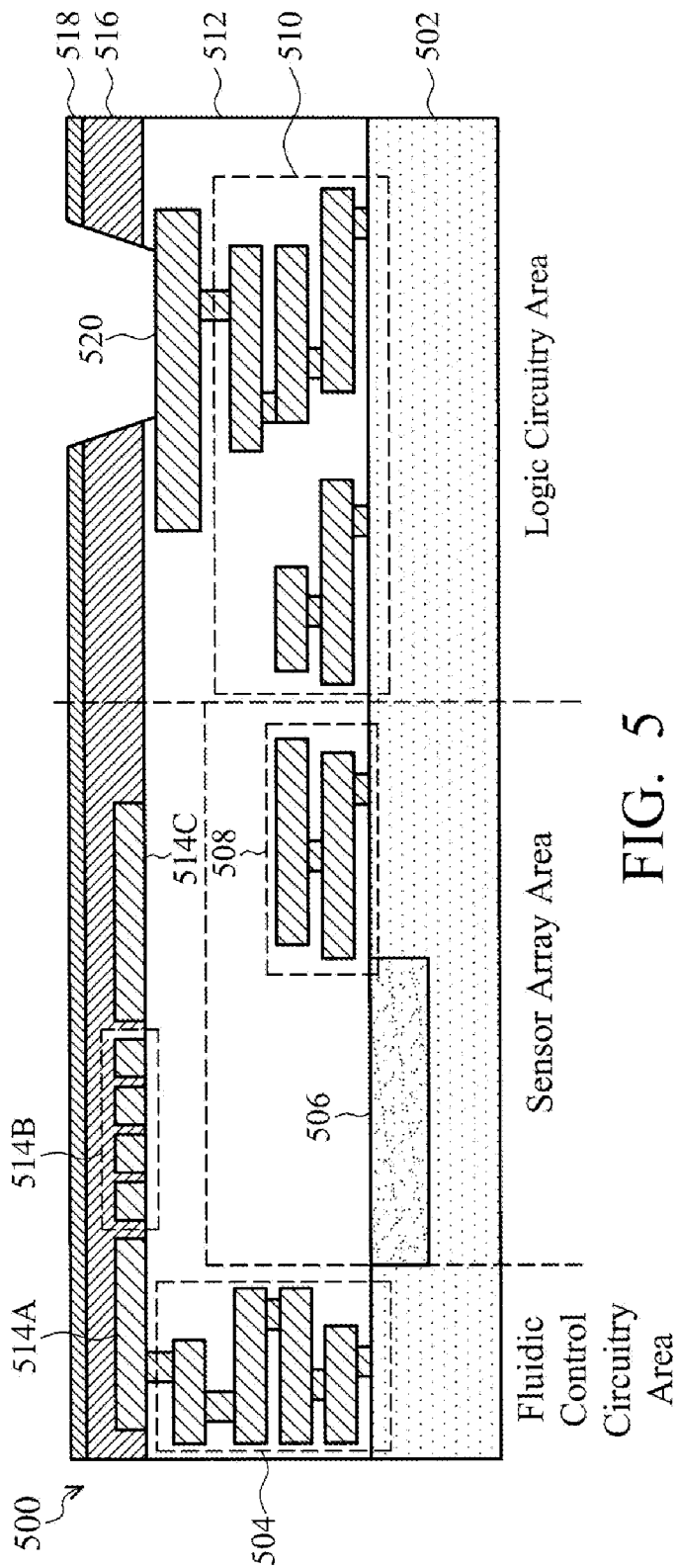
FIG. 5 is a cross-sectional diagram of a lower substrate for use in a bio-entity manipulation and processing system according to an embodiment.

FIG. 5 is a cross-sectional diagram of a lower wafer 500 for use in a microfluidic bio-entity manipulation and processing system. The lower wafer 500 includes four main functional areas: a fluidic control circuitry area, a solid-state based photosensor array area, a logic circuitry area, and a microfluidic channel area. The circuitry and photosensor array areas are formed on or in a substrate 502. As depicted, substrate 502 is a silicon substrate. However, in other embodiments, substrate 502 may be a substrate formed from another suitable elementary semiconductor, such as diamond or germanium; a suitable compound semiconductor, such as silicon carbide, indium arsenide, or indium phosphide; or a suitable alloy semiconductor, such as silicon germanium carbide, gallium arsenic phosphide, or gallium indium phosphide.

The fluidic control circuitry area includes fluidic control circuitry 504, which includes a plurality of metallization layers connected with associated transistors and other circuit components for programming and facilitating the path of droplet movement. The sensor array area includes a photosensor array 506 and photosensor control circuitry 508. In the depicted embodiment, the photosensor array 506 is an array of transistor-based photosensors and is a CMOS image sensor array. However, in other embodiments the photosensor array may include photodiodes, active pixel sensors, phototransistors, photoresistors, charged coupled devices, or the like. The photosensor array 506 is controlled by the photosensor control circuitry 508, which also includes a plurality of transistors and other circuit components. Finally, in the logic circuitry area, there is a significant amount of logic circuitry 510, including transistors and other circuit components. The logic circuitry 510 allows for input to and output from the lower wafer 500. Further logic circuitry 510 is coupled to both the photosensor control circuitry 508 and the fluidic control circuitry 504, to provide both with signal processing for optimal operation, such as analog-to-digital and digital-to-analog conversion. Fluidic control circuitry 504, photosensor control circuitry 508, and logic circuitry 510 are embedded in an inter-metal dielectric layer (IMD) 512.

On top of the IMD 512, is a plurality of bottom electrodes, much like the bottom electrodes of FIG. 2. Included in FIG. 5, three bottom electrodes are depicted: bottom electrodes 514A, 514B, and 514C. Many more electrodes may be present in practice, but the three depicted are adequate for clear discussion of lower wafer 500. In the depicted embodiment, bottom electrodes 514A, 514B, and 514C are made from an aluminum-copper alloy. However, in other embodiments different materials may be used that are also suitable for electrodes. Bottom electrodes 514A and 514C are solid rectangles as viewed from above, however the bottom electrode 514B is not. This will be discussed further with reference to FIG. 6. In FIG. 5, only the bottom electrode 514A appears to be connected to the fluidic control circuitry metallization stack. However, all bottom electrodes 514A, 514B, and 514C are in communication with the fluidic control circuitry 504, and thus all may be in an ON or OFF state as described in connection with FIG. 3.

On top of and surrounding the sides of bottom electrodes 514A, 514B, and 514C is a dielectric layer 516. In the depicted embodiment, dielectric layer 516 is a high-k dielectric layer formed by an atomic layer deposition (ALD) process, or a chemical vapor deposition (CVD) process, then followed by an annealing process. Over the dielectric layer 516 is a hydrophobic coating 518. In the depicted embodiment, hydrophobic coating 518 is made from polytetrafluoroethylene (PTFE), while in other embodiments it is a self-assembled monolayer. Also depicted in FIG. 5 is a contact pad 520 that is provided by etching through a portion of the hydrophobic coating 518, the dielectric layer 516, and a thickness of IMD 512. Other embodiments may feature additional metal layers and other variations, but in any embodiment, contact pad 520 may be provided to allow power or ground to be supplied to the lower wafer 500, or to allow for signal/control input or output.

Figure 6:
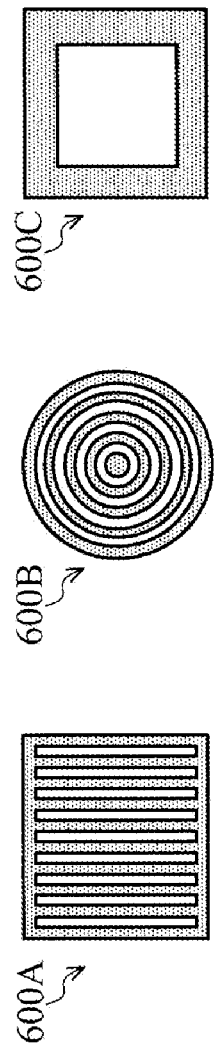
FIG. 6 provides top views of three optical components that may be used in a bio-entity manipulation and processing system according to an embodiment.

FIG. 6 provides top views of three variations of bottom electrode 514B that also serve as optical components that may be used in a bio-entity manipulation and processing system. Thus, in the depicted embodiments, optical components 600A, 600B, and 600C are made from aluminum. Other embodiments may be made from other materials. Optical component 600A is a rectangular grating, including a plurality of regular holes through a rectangular plate. By controlling the proximity and dimensions of the rectangular holes, optical component 600A may separate certain wavelength of light. This may aid in DNA sequencing because some tags generate light at a specific, identifiable frequency when removed. Background noise may be decreased by use of optical component 600A as bottom electrode 514B.

Optical component 600B is a plurality of concentric rings, with regular spacing in between each ring. Using the optical component 600B or other similar component as the bottom electrode 514B may allow for the concentration of light onto the sensor array. Additionally, optical component 600C may be used as the bottom electrode 514B. Optical component 600C may be a pass-through structure that simply allows light to pass through naturally from above the lower wafer 500 down onto the photosensor array 506. Optical component 600C may serve to limit off-axis light from being detected by the photosensor array 506. Other optical components may be used as desired in order to provide optical interference, diffraction, grating, and spectrophotometric functions for biooptical applications. Optical components 600A, 600B, and 600C are but a few examples. Other embodiments may include a transparent conductor, such as an indium tin oxide (ITO), as the bottom electrode 514B.

Figure 7:
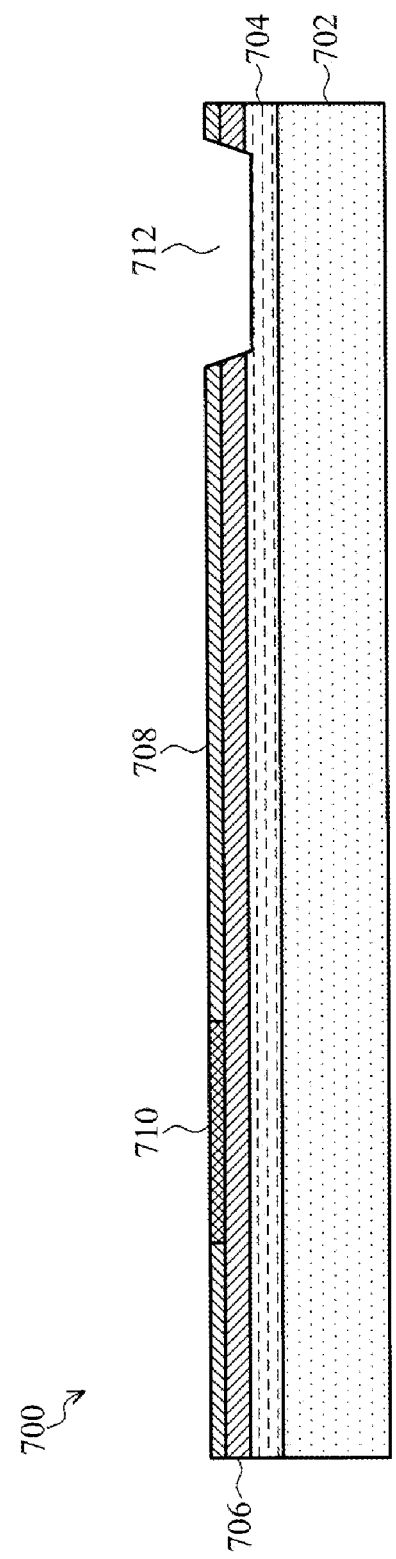
FIG. 7 is a cross-sectional diagram of an upper substrate that may be used in a bio-entity manipulation and processing system according to an embodiment.

FIG. 7 is a cross-sectional diagram of an upper wafer 700 that may be used in a bio-entity manipulation and processing system. The upper wafer 700 includes a substrate 702. In the depicted embodiment, substrate 702 is a glass wafer. However, in other embodiments, substrate 702 may be one of the materials mentioned above in alternate embodiments of substrate 502 of lower wafer 500 in FIG. 5. Over substrate 702 is a top electrode 704. In the depicted embodiment, top electrode 704 is an ITO layer. However, in other embodiments, top electrode 704 may be an aluminum layer or another suitable electrode layer.

A dielectric layer 706 is deposited over the top electrode 704. In this example, the dielectric layer 706 is a high-k dielectric layer that has been deposited by an ALD process before being annealed. Additionally, on top of the dielectric layer 706 is a hydrophobic coating 708. In the depicted embodiment, the hydrophobic coating 708 is made from PTFE, but in other embodiments the hydrophobic coating 708 is made from a self-assembling monolayer. A portion of the hydrophobic coating 708 has been treated with a surface treatment for labeling target DNA fragments, to create a surface treated area 710. In the depicted embodiment, the surface treated area 710 may promote DNA binding, while in other embodiments, an antibody binding surface treatment may be applied. The surface treated area 710 allows identifiable reactions to take place that give off light when a droplet containing components that react with the particular surface treatment is brought into contact with the surface treated area 710. For example, a molecular tag may be added onto base pairs that combine with the target DNA fragment, releasing the tag upon combination, with the release of the tag emitting a light signal.

FIG. 7 also depicts a contact pad area 712. Contact pad area 712 may be formed simply by etching away a portion of the hydrophobic coating 708 and the dielectric layer 706 so that electrical contact may be made with an exposed portion of the top electrode 704. In other embodiments, additional contacting layers may be deposited over the exposed portion of the top electrode 704 to facilitate wire bonding.

Figure 8:
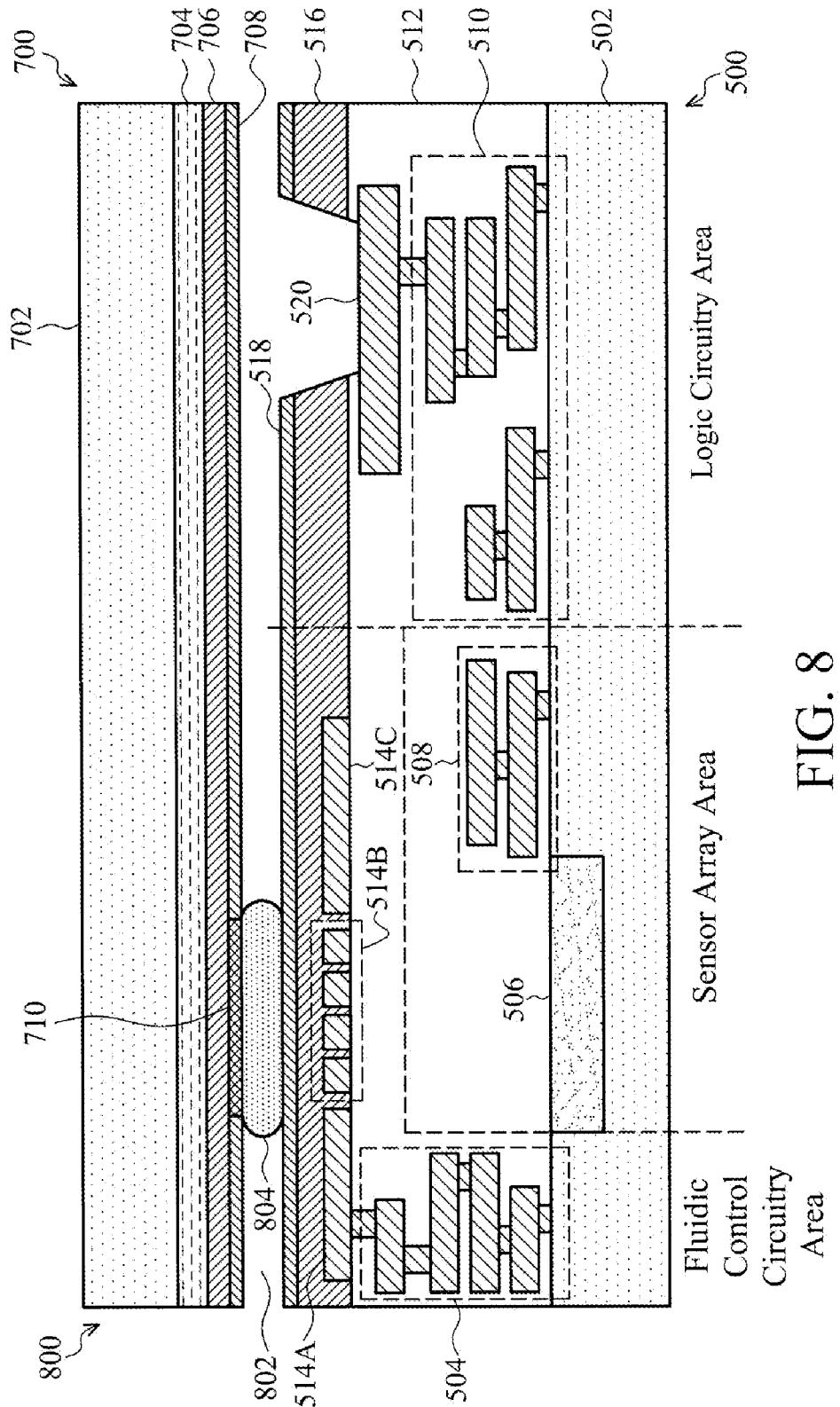
FIG. 8 is a cross-sectional diagram of a microfluidic bio-entity manipulation and processing system according to an embodiment.

FIG. 8 is a cross-sectional diagram of an integrated microfluidic bio-entity manipulation and processing system 800 that integrates the lower wafer 500 of FIG. 5 and the upper wafer 700 of FIG. 7. Thus FIG. 8 includes the substrate 502, with the fluidic control circuitry 504, the photosensor control circuitry 508, and the logic circuitry 510 thereon, in addition to the photosensor array 506 therein. An IMD 512 surrounds those features, and the integrated lower wafer 500 includes bottom electrodes 514A, 514B, and 514C deposited thereon with an overlying dielectric layer 516. On top of the dielectric layer 516 is a hydrophobic coating 518 that serves as the bottom of a microfluidic channel 802.

The microfluidic bio-entity manipulation and processing system 800 also includes substrate 702, which in this embodiment is a glass substrate. Over substrate 702 are a top electrode 704, a dielectric layer 706, and a hydrophobic coating 708. While the depicted embodiment of microfluidic bio-entity manipulation and processing system 800 does not depicted the contact pad area 712 of FIG. 7, other embodiments may contain such a feature. The hydrophobic coating 708 includes a surface treated area 710. The lower wafer 500 and upper wafer 700 are combined using die-level or wafer-level packaging techniques so that the surface treated area 710 is aligned with the photosensor array 506 and so that the hydrophobic coatings 518 and 708 are brought close together, without contacting, to form the microfluidic channel 802. While in the depicted embodiment the surface treated area 710 is formed on hydrophobic coating 708, in other embodiments surface treated area 710 may be formed on hydrophobic coating 518 of lower wafer 500 instead, which may improve performance by bringing the surface treated area 710 closer to photosensor array 506.

In operation, a droplet 804 is brought into contact with the surface treated area 710 using the actions depicted in FIG. 3, such as the lateral movement 300A. The droplet 804 includes a tagged bio-entity sample, such as DNA mixed with a reagent droplet such as the exemplary adenine reagent droplet 408B from FIG. 4. When the droplet 804 contacts the surface treated area 710, chemical reactions may remove the tag from the bio-entity samples in the droplet. The removal of the tag may enhance or intensify a photonic emission. The emission passes through the bottom electrode 514B, which in this embodiment is in the form of the optical component 600A of FIG. 6, and then is sensed in the photosensor array 506. This signal is captured by the photosensor control circuitry 508, and transmitted to the logic circuitry 510 for signal processing. Depending on the frequency or color of the photonic emission, a specific base pair may be detected. In embodiments, in which antibodies in the droplet 804 are being tested, the emission may indicate the presence of the particular antibody in the bio-entity sample in droplet 804. After the droplet 804 has been processed in this manner, it may be moved out of the microfluidic channel 802, and may be moved out of the microfluidic grid 400.

As seen in FIG. 8, the microfluidic bio-entity manipulation and processing system 800 provides microfluidic control circuitry 504 (with associated bottom electrodes 514A, 514B, and 514C), logic circuitry 510, and photosensor array 506, and photosensor control circuitry 508, on a single wafer, lower wafer 500. The lower wafer 500 also provides for a bottom surface of a microfluidic channel. The upper wafer 700, bonded to the lower wafer 500, provides the top surface of the microfluidic channel and the top electrode 704. In the depicted embodiment, with high-k dielectric layers 706 and 516, an electric potential of about 5 volts may be used to move and manipulate droplets like droplet 804, as well as power the various circuitry components for image sensing and processing, all on a single chip package.

Figure 9:
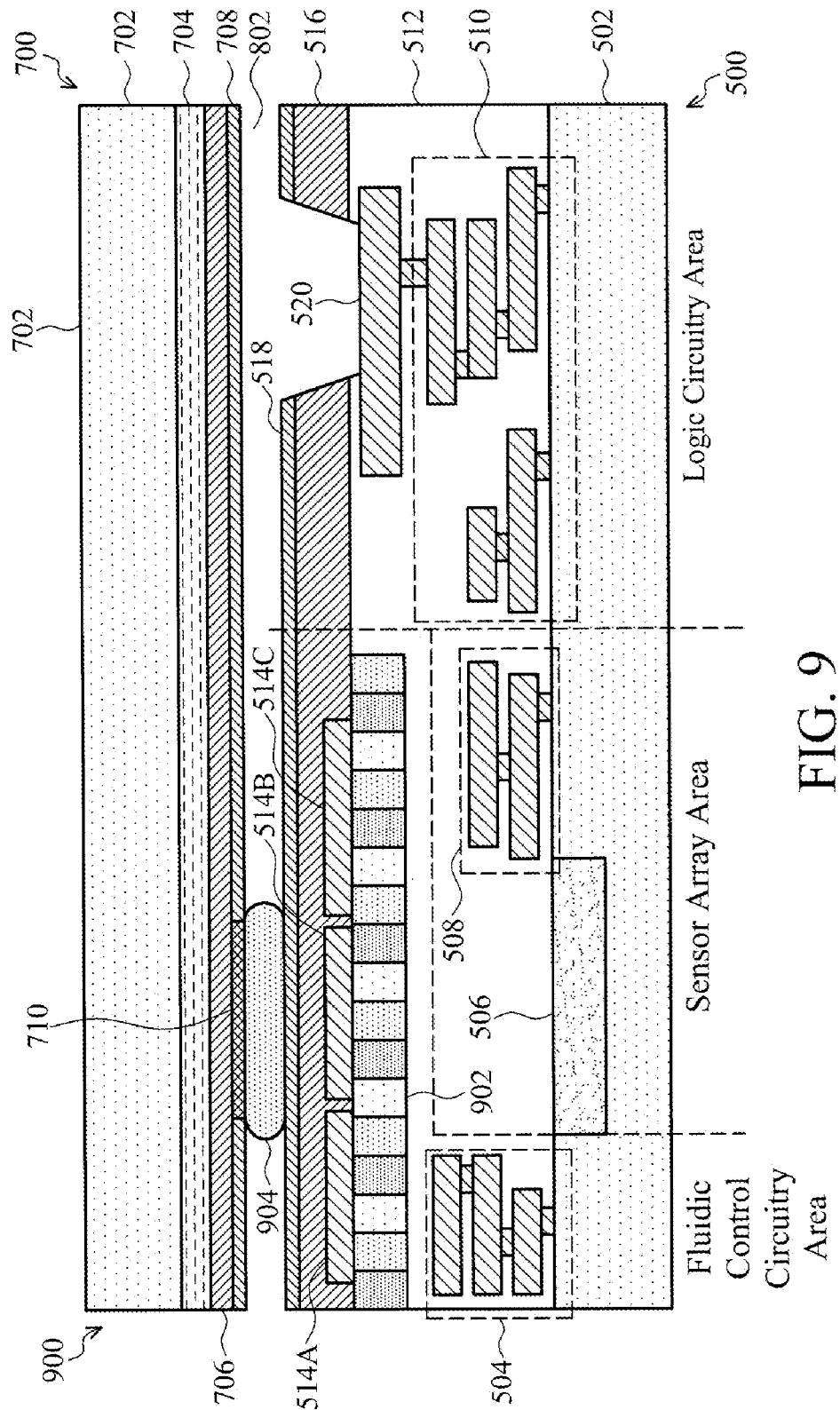
FIG. 9 is a cross-sectional diagram of a microfluidic bio-entity manipulation and processing system according to an additional embodiment that includes a color filter array.

FIG. 9 is a cross-sectional diagram of an integrated microfluidic bio-entity manipulation and processing system 900 according to an additional embodiment that includes a color filter array. Several features are common between the microfluidic bio-entity manipulation and processing system 900 and the microfluidic bio-entity manipulation and processing system 800 of FIG. 8. Such common features are commonly numbered to avoid unnecessary repetition in this disclosure. Underneath the bottom electrodes 514A, 514B, and 514C is a color filter array (CFA) 902, with a plurality of red, blue, and green filters. As depicted in FIG. 9, the bottom electrode 514B is configured as the optical component 600C of FIG. 6. Thus, when an emission is caused by the removal of tag from a bio-entity sample droplet 904 by a reaction at the surface treated area 710, the path passes through the opening of the bottom electrode 514B, through the CFA 902 before entering the photosensor array 506 where the emission can be detected. The addition of the CFA 902 may allow for the more traditional methods of detecting the color of emissions. By detecting the color of the emissions, the particular tag being removed by the reaction at the surface treated area 710 can be identified. In this manner, DNA fragments may be sequenced and specific pathogens may be detected.

While in the depicted embodiment the surface treated area 710 is formed on hydrophobic coating 708 of upper wafer 700, in other embodiments surface treated area 710 may be formed on hydrophobic coating 518 of lower wafer 500 instead, which may improve performance by bringing the surface treated area 710 closer to photosensor array 506.

Figure 10:
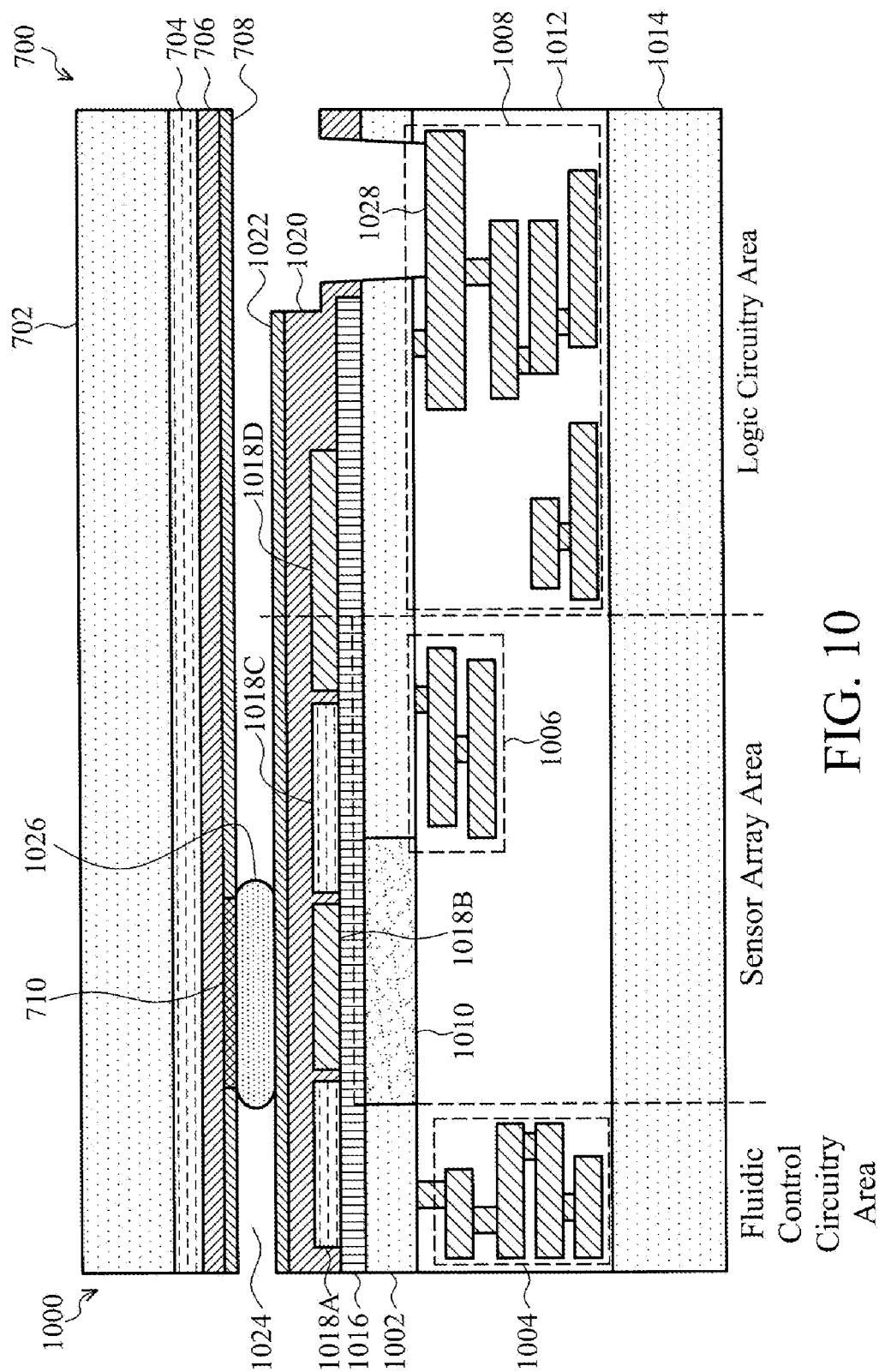
FIG. 10 is a cross-sectional diagram of a lower substrate of a microfluidic bio-entity manipulation and processing system according to an embodiment that utilizes back-side exposure.

FIG. 10 is a cross-sectional diagram of an integrated microfluidic bio-entity manipulation and processing system 1000 according to an additional embodiment that utilizes back-side illumination. The lower wafer of system 1000 is fabricated on a substrate 1002. In the depicted embodiment, substrate 1002 is a P-type silicon substrate, but in other embodiments it may be other materials as described above. During fabrication, a plurality of metal layers is deposited to form fluidic control circuitry 1004, photosensor control circuitry 1006, and logic circuitry 1008. A plurality of photodetectors are fabricated in substrate 1002 to create a photosensor array 1010 that is in communication with photosensor control circuitry 1006. After an IMD 1012 has covered the control and logic circuitries, the material stack on substrate 1002 is bonded to a carrier wafer 1014. Carrier wafer 1014 is a silicon wafer in the depicted embodiment, but may be a glass or other material wafer in other embodiments.

After bonding the carrier wafer 1014 to the top of IMD 1012, the bonded wafers are flipped, and the back side of the substrate 1002 is thinned. In the present embodiment, a high selectivity wet etching process using hydrofluoric, nitric, and acetic acids (HNA) is used to thin substrate 1002. In an alternative embodiment, a chemical mechanical planarization (CMP) process may be used to thin substrate 1002. After the thinning process the photodetectors in the photosensor array 1010 are close to the back side surface of substrate 1002. This may decrease the overall stack height between the photosensor array 1010 and the source of emissions, thereby improving performance.

An anti-reflective coating (ARC) 1016 is deposited and patterned on top of the back side of substrate 1002. In the depicted embodiment, ARC 1016 may be a silicon oxide ARC layer. After the ARC 1016 is patterned a plurality of bottom electrodes may be deposited. FIG. 1000 depicts four bottom electrodes: bottom electrodes 1018A, 1018B, 1018C, and 1018D. In the depicted embodiment, bottom electrodes 1018A and 1018C are transparent bottom electrodes, made from ITO. Meanwhile, bottom electrode 1018B and 1018D are back side metal electrodes made of an aluminum-copper alloy. Other configurations and materials may be used for the bottom electrodes 1018A, 1018B, 1018C, and 1018D in other embodiments. In embodiments where more than one material is used for the bottom electrodes, different processes will be used for deposition and patterning. In general, a portion of the photosensor array 1010 is covered by an opaque material, which in the depicted embodiment is provided by bottom electrode 1018B. This opaque material is used as a dark reference, to determine the amount of signal from the photosensor 1010 that is attributable to sources other than visible light, such as heat.

A dielectric layer 1020 is deposited on top of the bottom electrodes, as well as the exposed portions of ARC 1016 and the back side of substrate 1002. In the depicted embodiment, the dielectric layer 1020 is a high-k dielectric layer, deposited by an ALD process and then annealed, while in other embodiments dielectric layer 1020 is deposited by a CVD before annealing. Over the dielectric layer 1020, a hydrophobic coating 1022 is deposited. Hydrophobic coating 1022 provides the bottom half of a microfluidic channel 1024, through which a droplet 1026 may be moved. In the depicted embodiment, the hydrophobic coating 1022 is made from PTFE. In other embodiments, it may be a self-assembling monolayer. Also depicted in FIG. 10 is a contact pad 1028 formed by etching through the hydrophobic coating 1022, the dielectric layer 1020, through substrate 1002 and a portion of IMD 1012. Contact pad 1028 provides a location for wire bonding to allow for input and output as well as a power supply connection to logic circuitry 1008 and other circuitry embedded in IMD 1012.

The wafer based on lower substrate 1002 is bonded to an upper wafer, like upper wafer 700 of FIG. 7. Thus, the upper wafer 700 includes a substrate 702, a top electrode 704, a dielectric layer 706, and a hydrophobic coating 708 with a surface treated area 710. Along with the hydrophobic coating 1022, hydrophobic coating 708 forms the microfluidic channel 1024. As discussed with other embodiments herein, the droplet 1026 can be moved into contact with the surface treated area 710, which provides a site for characteristic biochemical interactions with bio-entities that emit light. These light emissions are detected by the photosensor array 1010 and then processed to determine the entities involved in the reaction. By determining these entities, a nucleotide base or a specific antibody may be registered. While in the depicted embodiment the surface treated area 710 is formed on hydrophobic coating 708, in other embodiments surface treated area 710 may be formed on hydrophobic coating 1022 of the wafer based on lower substrate 1002 instead, which may improve performance by bringing the surface treated area 710 closer to photosensor array 1010.

Figure 11:
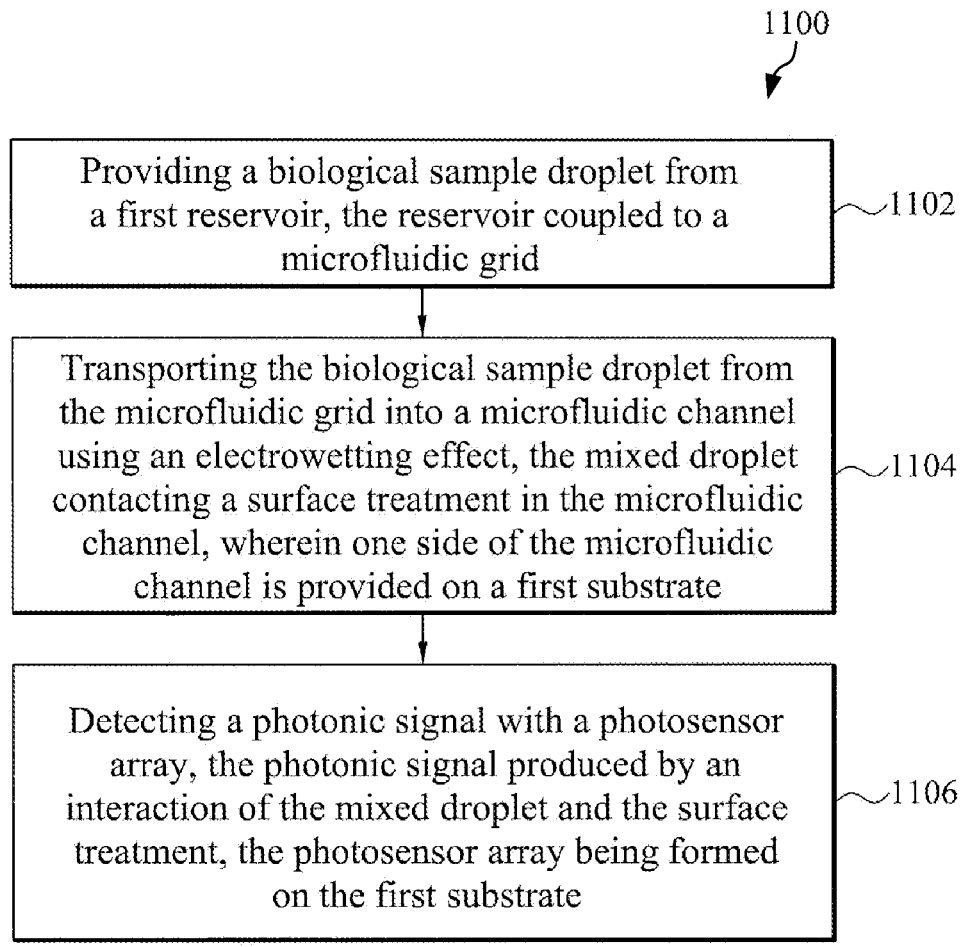
FIG. 11 is a flowchart of a method for manipulating and processing bio-entity samples with an integrated semiconductor device according to some embodiments.

FIG. 11 is a flowchart of a method 1100 for manipulating and processing bio-entity samples with an integrated semiconductor device. The method 1100 begins in step 1102 when a bio-entity sample droplet is obtained from a first reservoir. The first reservoir is coupled to a microfluidic grid. The method 1100 may continue in step 1104 when the bio-entity sample droplet is transported from the microfluidic grid into a microfluidic channel using an electrowetting effect. The microfluidic channel has a side provided on a first substrate. When in the microfluidic channel the bio-entity sample droplet contacts a surface treatment in the microfluidic channel. A biochemical reaction is triggered upon contact between the bio-entity sample droplet and the surface treatment. In step 1106, a photonic signal that is produced by the interaction of the bio-entity sample droplet and the surface treatment is detected by a photosensor array that is formed on the first substrate.

To better illustrate method 1100 in operation, reference will be made to the integrated microfluidic bio-entity manipulation and processing system 800 of FIG. 8 and some other figures discussed above such as FIG. 3 and FIG. 4. Method 1100 may also be explained with reference to other embodiments of integrated microfluidic bio-entity manipulation and processing systems disclosed here in. Thus, reference to FIG. 8 is made by way of non-limiting example. A sample tank or reservoir 410A of FIG. 4 may include a larger volume of a bio-entity sample. By using the action depicted as droplet formation 300D of FIG. 3, a bio-entity sample droplet 804 is formed from the larger volume and introduced into the microfluidic grid 400 of FIG. 4 (step 1102). The bio-entity sample droplet 804 is transported through microfluidic grid 400, which includes a plurality of microfluidic channels, one of which is microfluidic channel 802 of FIG. 8. Microfluidic channel 802 is located on top of a material stack deposited on substrate 502, the top layer of which, hydrophobic coating 518, supplies the bottom surface of the microfluidic channel 802. Transporting the bio-entity sample droplet 804 through the microfluidic channel is accomplished by using the logic circuitry 510 to control the fluidic control circuitry 504.

The bio-entity sample droplet 804 is moved through the microfluidic grid 400 of FIG. 4 and the microfluidic channel 802 of FIG. 8 by using the electrowetting effect. Bottom electrodes 514A, 514B, and 514C are asserted in either ON or OFF states as indicated by FIG. 3, in order to subject the biological droplet to controlled hydrophobic or hydrophilic surfaces according to the ON or OFF states of the bottom electrodes. By control of the bottom electrodes 514A, 514B, and 514C, and in conjunction with a top electrode 704, the bio-entity sample droplet 804 is guided into contact with the surface treated area 710, which has had a surface treatment applied to it (step 1104). Guiding the bio-entity sample droplet 804 into contact with the surface treated area 710 is accomplished by having the logic circuitry 510 exert control over the fluidic control circuitry 504.

Because of the surface treatment, surface treated area 710 and the bio-entity sample droplet 804 may undergo a biochemical reaction which intensifies or enhances the fluorescent light signal. This light passes through the bottom electrode 514B to a photosensor array 506. Photosensor 506 detects the light and a corresponding signal is sent to the logic circuitry 510 for processing (step 1106). Logic circuitry 510 may interpret the signal by color or frequency to determine the biochemical reaction that occurred. The biochemical reaction may indicate that a specific base nucleotide was detected in a target DNA fragment, or that a particular antibody was present in the bio-entity sample droplet. After the bio-entity sample droplet 804 has been processed, it may be removed from the microfluidic channel 802. In some embodiments a buffer droplet, such as buffer droplet 408A of FIG. 4, may be transported through the microfluidic channel 802 in order to clean it.

Additionally, in some embodiments of method 1100, an adenine reagent droplet 408B obtained from the adenine reagent tank 406A in FIG. 4 is combined with the bio-entity sample droplet 804, using the droplet merge 300C operation of FIG. 3. The droplet merge 300C operation may mix the bio-entity sample droplet 804 and the adenine reagent droplet 408B in the microfluidic grid 400. The mixed bio-entity sample droplet 804 may then be directed into contact with the surface treated area 710 in the microfluidic channel 802. In some embodiments, bottom electrode 514B may be an optical component in addition to acting as an electrode. Thus the bottom electrode 514B may be optical component 600A in one embodiment, and 600B in another embodiment. In other embodiments, a reagent other than the adenine reagent droplet 408B may be used to create a different mixed bio-entity sample droplet 804.

Figure 12A:
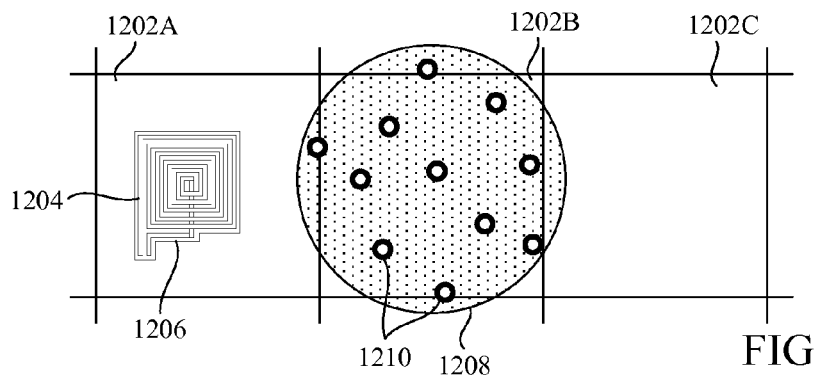
FIGS. 12A, 12B, 12C, and 12D are a series of diagrams illustrating how certain actions may be achieved using an electrowetting fluidic control system having a magnetic field generation device according to some embodiments.

FIGS. 12A, 12B, 12C, and 12D illustrate a process of manipulating droplets containing bio-entities according to some embodiments of the present disclosure that incorporate one or more magnetic field generation devices. FIGS. 12A-D may be understood in the context of FIG. 3, which illustrates several other manipulations of bio-entity containing droplets. A portion of a microfluidic grid, such as the microfluidic grid 400 of FIG. 4 is shown. For example, the portion shown may be a portion of a microfluidic channel. FIG. 12A illustrates electrodes 1202A, 1202B, and 1202C. These electrodes may be similar to the electrodes 208A, 208B, and 208C, illustrated in FIG. 3 and described above. In the depicted embodiment, the electrode 1202A further includes a magnetic field generation device 1204 positioned within an opening 1206 formed in the conductive material of the electrode 1202A.

The magnetic field generation device 1204 may be any device of a suitable scale that can generate a magnetic field. While further discussion is provided herein with respect to detailed aspects of the magnetic field generation device 1204, many embodiments of the magnetic field generation device 1204 may comprise a conductor configured in a coil shape through which a varying current can flow. As the current in the conductive material of the magnetic field generation device 1204 varies, under the control of fluidic control circuitry, a corresponding magnetic field is generated. As is described herein, the generated magnetic field may be used to manipulate droplets containing bio-entities by tagging target bio-entities with magnetic tags, referred to herein as magnetic beads.

FIG. 12A further illustrates a droplet 1208 positioned over the electrode 1202B. The droplet 1208 contains bio-entities as described herein. For example, the droplet 1208 may include DNA, RNA, antibodies, proteins, enzymes, small molecules, etc. As described herein, one or more bio-entities may be tagged with a fluorescent tag (not illustrated). For example, a tag may be provided to bind to a specific protein that may be present in the droplet 1208. The droplet 1208 includes a plurality of magnetic tags or magnetic beads 1210. The magnetic beads 1210 may be microbeads or nanobeads that can be bound to specific target bio-entities to facilitate the specific manipulation and/or identification of the targets. The magnetic beads may be formed from a metal or a non-metal. For example, the magnetic beads 1210 may be gold nanobeads. The magnetic beads may be responsive to a magnetic field or may produce a magnetic field. The magnetic beads may be made from a high magnetic moment material, such as platinum, or iron, nickel, cobalt, aluminum, copper, tungsten, manganese, lithium, alnico, or other such material.

Figure 12B:
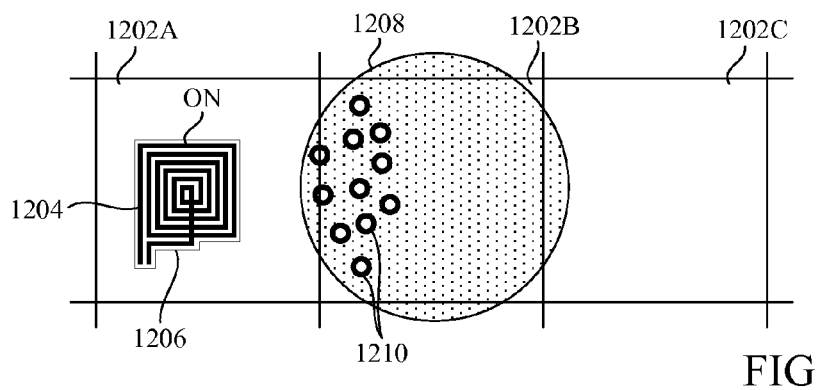

When the magnetic field generation device 1204 is activated, a magnetic field is produced that interacts with the magnetic beads 1210 as shown in FIG. 12B. FIG. 12B illustrates an embodiment in which the magnetic field generation device 1204 is activated, by fluidic control circuitry, to produce a magnetic field. The magnetic field may be a pulsed magnetic field or the magnetic field may be an oscillating magnetic field. The fluidic control circuitry may control the current flowing through the magnetic field generation device 1204 in order to produce a desired magnetic field, having a desired magnitude and a desired duration, etc. As shown in FIG. 12B, the magnetic beads 1210, bound to specific target bio-entities, are attracted by the magnetic field and pulled toward the magnetic field generation device 1204. This attractive force may cause the magnetic beads 1210, and thereby the targeted bio-entities bound thereto, to migrate to one side of the droplet 1208. In this way, the concentration of the target bio-entity may be increased on one side of the droplet 1208 relative to the other side of the droplet 1208. As shown, the concentration of magnetic beads 1210 is increased within the side of the droplet 1208 closest to the magnetic field generation device 1204, which is situated within the opening 1206 of the electrode 1202A, relative to the concentration of magnetic beads 1210 on the side of the droplet 1208 closest to the electrode 1202C.

In some embodiments, the attraction between the magnetic beads 1210 and the magnetic field generation device 1204 may be sufficient to pull the droplet 1208 away from its current position over the electrode 1202B to a new position over the electrode 1202A. This may be done by providing a sufficiently large change in the current flowing through the magnetic field generation device 1204. In this way, the magnetic field generation device 1204 may provide for the transportation of droplets, like the droplet 1208, through a microfluidic grid. Accordingly, in some embodiments of the microfluidic grid 400, rather than include electrodes like the electrodes 1202A-C, include a plurality of magnetic field generation devices that are combined to form a steerable grid including a plurality of channels. Other embodiments, such as those illustrated in FIGS. 12A-D, both magnetic field generation devices and electrodes are included in the microfluidic grid.

Figure 12C:
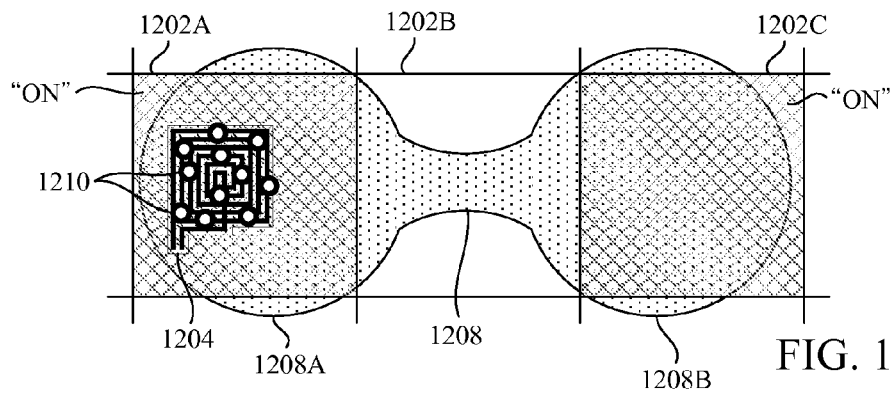

FIG. 12C illustrates the concentration and separation step of the operation. As shown in FIG. 12C, the electrodes 1202A and 1202C are asserted into an ON state by fluidic control circuitry, causing the area in the microfluidic channel above these electrodes to effectively change in hydrophobicity, becoming relatively hydrophilic compared with the unasserted electrode 1202B. In consequence, the droplet 1208 is pulled away from the area defined by the electrode 1202B and toward both of the electrodes 1202A and 1202C as shown. Because the droplet 1208 is pulled in two opposing directions simultaneously, a portion of the droplet 1208 (referred to as portion 1208A) is pulled to the left, as seen in FIG. 12C, while another portion (referred to as portion 1208B) is pulled to the right. In the embodiment depicted in FIG. 12C, the magnetic field generation device 1204 is also in an activated or asserted state by the fluidic control circuitry such that the magnetic beads 1210 are attracted to the magnetic field generation device 1204 and concentrate thereover.

In some embodiments, the magnetic field generation device 1204 may not be active at the time that the electrodes 1202A and 1202C are activated. For example, after the magnetic beads 1210 have been attracted within the droplet 1208 toward the electrode 1202A by the magnetic field generation device 1204, the fluidic control circuitry may cause the magnetic field generation device 1204 to stop generating a magnetic field. The electrodes 1202A and 1202C may then be activated to split the droplet 1208. As long as the electrodes 1202A and 1202C are activated before the magnetic beads 1210 have re-dispersed within the droplet 1208, either all or a majority of the magnetic beads 1210 (and the bio-entities tagged therewith) may be included in the droplet portion 1208A. In this way, the droplet portion 1208A includes a higher concentration of magnetic beads 1210 than the droplet portion 1208B.

Figure 12D:
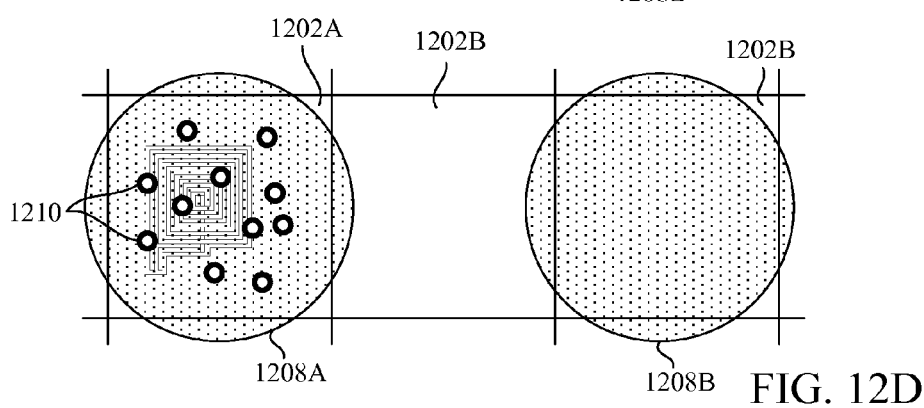

As shown in FIG. 12D, the droplet portions 1208A and 1208B are stabilized over the electrodes 1202A and 1202B, respectively, and the electrodes 1202A and 1202B are turned off. In some embodiments, the electrodes may continue to be asserted in order to maintain the droplet portions 1208A and 1208B in position. After the magnetic field generation device 1204 is deactivated or reverted to an OFF state the magnetic beads 1210 may be dispersed throughout the droplet portion 1208A. Because the droplet portions 1208A and 1208B are derived from the droplet 1208, the combined volumes of the droplet portions 1208A and 1208B is equal to the original volume of the droplet 1208. Because the magnetic beads 1210 are all or mostly contained in the droplet portion 1208A, the concentration of the magnetic beads 1210 per unit volume is now higher than the concentration of the original droplet 1208. The concentration is also higher than in the droplet portion 1208B. Because the concentration of magnetic beads 1210 is higher, the concentration of bio-entities tagged using the magnetic beads 1210 is also higher. In this way, magnetic field generation device 1204 may be used to concentrate and separate target bio-entities from a sample droplet. Other, non-tagged bio-entities contained in the droplet 1208 may be unaffected by the magnetic field generation device 1204. The concentrations of such non-tagged bio-entities may be substantially equal in the droplet portions 1208A and 1208B.

While the embodiment shown in FIGS. 12C and 12D indicate that all of the magnetic beads 1210 are contained in the droplet portion 1208A. In other embodiments, some magnetic beads 1210 may be contained in the droplet portion 1208B after the droplet 1208 is separated. Such an embodiment still increases the relative concentration of tagged bio-entities, by increasing the number of tagged bio-entities in a droplet portion while decreasing the overall volume of the droplet portion. By concentrating the tagged bio-entities, a sample may be prepared for further analysis such as fluorescent detection using a photosensor. Additionally, multiple droplets like the droplet 1208 may be concentrated by separation into multiple droplet portions, the more highly concentrated portions can then be combined in the microfluidic grid to provide a larger volume droplet that also exhibits a higher concentration of the target tagged bio-entities (tagged by the magnetic beads 1210).

In some embodiments, the electrodes 1202A-C and other electrodes present in an integrated bio-entity manipulation and processing device may be about 2 millimeters by about 2 millimeters in geometry. In such embodiments, the magnetic field generation device 1204 may occupy an area of about 1 millimeters by about 1 millimeters. In other embodiments, the magnetic field generation device 1204 may be about 0.1 millimeters by about 0.1 millimeters in area. Other dimensions of the electrodes and oath magnetic field generation devices used in such manipulation and processing devices are within the scope of this disclosure.

FIG. 13 presents a cross-sectional diagram of a microfluidic bio-entity manipulation and processing system 1300, according to some additional embodiments that include a magnetic field generation device. The system 1300 includes a lower wafer 1301 for use in a microfluidic bio-entity manipulation and processing system. The lower wafer 1301 may include four main functional areas: a fluidic control circuitry area, a solid-state based photosensor array area, a logic circuitry area, and a microfluidic channel area. Some embodiments of the system 1300 may not include the photosensor array area. The circuitry and photosensor array areas (when present) are formed on or in a substrate 1302. As depicted, substrate 1302 is a silicon substrate. However, in other embodiments, substrate 1302 may be a substrate formed from another suitable material, such as diamond or germanium; a suitable compound semiconductor, such as silicon carbide, indium arsenide, or indium phosphide; or a suitable alloy semiconductor, or such as silicon germanium carbide, gallium arsenic phosphide, or gallium indium phosphide.

The fluidic control circuitry area includes fluidic control circuitry 1304, which includes a plurality of metallization layers connected with associated transistors and other circuit components for programming and facilitating of droplet movement, concentration, and/or separation. The sensor array area includes a photo sensor array 1306 and photosensor control circuitry 1308. In the depicted embodiment, the photosensor array 1306 is an array of transistor-based photosensors and is a CMOS image sensor array. However, in other embodiments the photosensor array 1306 may include photodiodes, active pixel sensors, phototransistors, photoresistors, charged coupled devices, or the like. The photosensor array 1306 is controlled by the photosensor control circuitry 1308, which also includes a plurality of transistors and other circuit components. Finally, in the logic circuitry area includes transistors and other circuit components. The logic circuitry 1310 allows for input to and output from the lower wafer 1301. Further logic circuitry 1310 may be coupled to the photosensor control circuitry 1308 and/or the fluidic control circuitry 1304, to provide both with signal processing for optimal operation, such as analog-to-digital and digital-to-analog conversion and to provide an interface for these components. Fluidic control circuitry 1304, photosensor control circuitry 1308, and logic circuitry 1310 may be embedded in an inter-metal dielectric layer (IMD) 1312.

On top of the IMD 1312, is a plurality of bottom electrodes, much like the electrodes 1202A-C illustrated in FIG. 12 and described herein. Included in FIG. 13, three bottom electrodes are depicted: electrodes 1314A (a portion of which is shown), 1314B, and 1314C. Many more electrodes may be present in practice, but the three depicted are adequate for clear description of lower wafer 1301. The electrode 1314B includes a magnetic field generation device 1315. The magnetic field generation device 1315 may be situated in an opening in the electrode 1314B, as illustrated by the opening 1206 in the electrode 1202A of FIGS. 12A-D. Because of its shape, the magnetic field generation device 1315 may also serve as an optical component, like the optical components 514B, 600A, 600B, and 600C as described herein in connection with the components, systems, and methods of FIGS. 5, 6, 8, and 11. Thus, the magnetic field generation device 1315 may function as both a magnetic field generator and as an optical component in some embodiments.

In the depicted embodiment, electrodes 1314A and 1314C are made from an aluminum-copper alloy. However, in other embodiments different materials may be used that are also suitable for electrodes. In some embodiments, the magnetic field generation device 1315 may be formed from the same material. However, in other embodiments a different material may be used for the magnetic field generation device than for the electrodes 1314A and 1314C. As shown, the outer portion of the electrode 1314B (i.e. the portion having the opening therein) is formed from the aluminum-copper alloy. The magnetic field generation device 1315 is made from a cobalt-iron alloy. In other embodiments, a platinum-manganese alloy may be used. In other embodiments a combination of cobalt-iron and platinum-manganese alloys may be employed. In general, conductive, CMOS-compatible materials may be used. Electrodes 1314A and 1314C may be solid rectangles as viewed from above or have some other shape. As described, the electrode 1314B includes an opening that contains the magnetic field generation device 1315. In FIG. 13, only the bottom electrode 1314A appears to be connected to the metallization stack of the fluidic control circuitry 1304. However, all of the electrodes 1314A, 1314B, and 1314C are in communication with the fluidic control circuitry 1304, and thus all may be set to an ON or OFF state as described in connection with FIG. 12. Similarly, the magnetic field generation device 1315 is illustrated as coupled to the metallization layers and other features of the fluidic control circuitry 1304 so that it may be controlled in an ON or OFF state as desired and to control the magnetic field created thereby.

On top of and surrounding the sides of bottom electrodes 1314A, 1314B, and 1314C is a dielectric layer 1316. In the depicted embodiment, dielectric layer 1316 is a high-k dielectric layer formed by an atomic layer deposition (ALD) process, or a chemical vapor deposition (CVD) process, then followed by an annealing process. Over the dielectric layer 1316 is a hydrophobic coating 1318. In the depicted embodiment, hydrophobic coating 1318 is made from polytetrafluoroethylene (PTFE), while in other embodiments it may be a self-assembled monolayer. Also depicted in FIG. 13 is a contact pad 1320 that is provided by etching through a portion of the hydrophobic coating 1318, the dielectric layer 1316, and a thickness of IMD 1312. The contact pad 1320 and other similar pads on the lower substrate 1301 may provide power or ground to be supplied to the lower wafer 1301, or to allow for signal/control input or output.

The system 1300 depicted in FIG. 13 further contains a portion of a hydrophobic coating 1319 as would be present on an upper substrate (not otherwise shown), like the upper wafer 700 of FIG. 7. In some embodiments, a portion of the hydrophobic coating 1318 has been treated with a surface treatment for labeling target DNA fragments, to create a surface treated area 1322. In the depicted embodiment, the surface treated area 1322 may promote DNA binding, while in other embodiments, an antibody binding surface treatment may be applied. The surface treated area 1322 may allow identifiable reactions to take place that produce light when a droplet containing components that react with the particular surface treatment are brought into contact with the surface treated area 1322. For example, a molecular tag may be added onto base pairs that combine with the target DNA fragment, releasing the tag upon combination, with the release of the tag emitting a light signal. In some embodiments, a target bio-entity may be tagged with a magnetic bead as well as other tags for other purposes such as identification and quantification. In some instances, the magnetic bead tags may also be used for such purposes.

In between the hydrophobic coating 1319 of the upper substrate and the hydrophobic coating 1318 of the lower substrate 1301, a microfluidic channel 1324 is formed. The microfluidic channel 1324 may be part of a microfluidic grid, such as the microfluidic grid 400 of FIG. 4. As illustrated, a droplet 1326 is present in the microfluidic channel 1324 and includes a plurality of tagged bio-entities that are tagged with the magnetic beads 1328, like the magnetic beads 1210 of FIGS. 12A-D. In some embodiments the magnetic beads 1328 may be microbeads or nanobeads made from platinum or from a platinum containing alloy. In some embodiments, the magnetic field generation device is made from a high magnetic moment material, such as platinum, or iron, nickel, cobalt, aluminum, copper, tungsten, manganese, lithium, alnico, or other such material. The beads may range in diameter from about 20 nanometers to about 50 microns. As discussed, the magnetic beads may be bound to different bio-entities for different applications such as identification, quantification, separation, concentration, etc.

By varying the current through the magnetic field generation device 1315, the magnetic beads 1328, and thereby the tagged target bio-entities, within the droplet 1326 may be attracted to toward the magnetic field generation device 1315 for concentration and/or separation as shown in FIGS. 12A-D. The electrodes 1314A-C may be changed from ON states to OFF states, etc., in order to alter the hydrophobicity of portions of the channel 1324 to move the droplet 1326 as desired.

FIGS. 14A, 14B, and 14C are top view diagrams of magnetic field generation devices 1400A, 1400B, and 1400C, such as may be used to provide the magnetic field generation devices 1204 and 1315 of FIGS. 12A-D and 13, respectively, according to some embodiments. The area occupied by the magnetic field generation devices 1400A-C may vary from more than 1 millimeter by 1 millimeter to less than 0.1 millimeters by 0.1 millimeters. As shown in FIG. 14A, the magnetic field generation device 1400A has a generally square shape, although other rectangular shapes may be present in some embodiments. The magnetic field generation device 1400A includes a coil of material 1402 having a first end and a second end coupled to fluidic control circuitry. The fluidic control circuitry may be used to drive a current through the coil of material 1402, thereby generating a magnetic field as the current driven through the coil of material 1402 changes. The current may be pulsed, or the current may be provided by an alternating current. Also shown in FIG. 14A is a magnetic core 1404 which may be positioned, in some embodiments, in the center of the coil of material 1402 so as to amplify the effect of the varying current when it flows and varies therethrough. FIGS. 14B and 14C depict alternative embodiments of magnetic field generation devices in magnetic field generation devices 1400B and 1400C. The magnetic field generation device 1400B has a generally hexagonally-shaped coil of material 1406, while the magnetic field generation device 1400C has a generally circular-shaped coil of material 1408. Both of the coil of material 1406 and the coil of material 1408 may be characterized as having an outer diameter D1 and an inner diameter D2. Similarly, the coils of material 1402, 1406, and 1408, include a coil thickness T1 and a coil gap G1. In general, the magnitude of magnetic field produced by a current flowing through each of the coils of material 1402, 1406, and 1408, may be proportional to the number of turns or loops therein, such that more loops may be better than fewer. Because the coils of material 1402, 1406, and 1408 may be fabricated using CMOS compatible materials, the thickness T1 and gap G1 of a coil may permit a large number of loops. For example, the thickness may range from about 10 microns to about 1000 microns and the gap G1 may range from about 100 nanometers to about 5 nanometers.

Figure 15A:
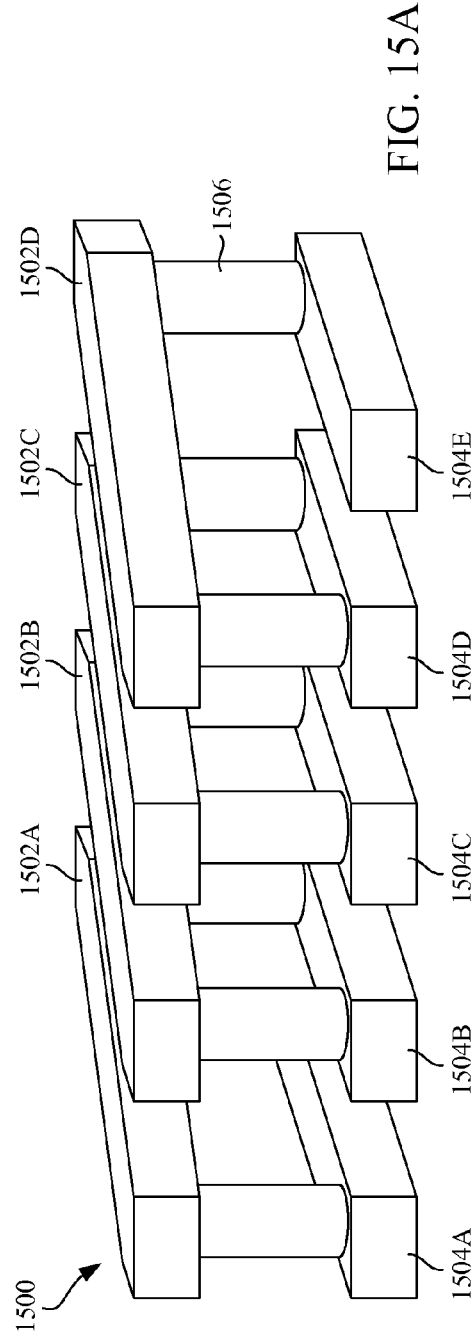
FIGS. 15A and 15B are a perspective view diagram and a top view diagram, respectively, of another magnetic field generation device according to some embodiments.
Figure 15B:
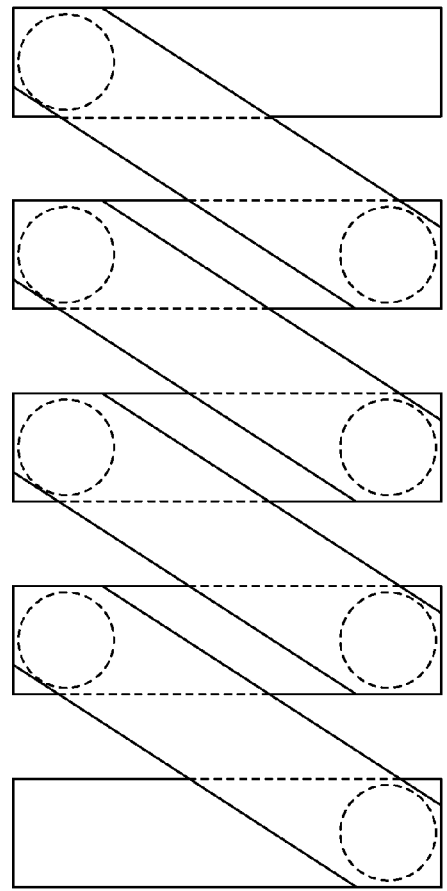

FIGS. 15A and 15B are a perspective view diagram and a top view diagram, respectively, of another magnetic field generation device 1500 according to some other embodiments. The magnetic field generation device 1500 may be included as the magnetic field generation device 1315 positioned within the electrode 1314B as seen in FIG. 13 and described above. The magnetic field generation device 1500 differs from the magnetic field generation devices 1400A-C in that the magnetic field generation device 1500 produces a horizontally aligned magnetic field. As illustrated in FIG. 15A, the magnetic field generation device 1500 includes a plurality of upper bars 1502A, 1502B, 1502C and 1502D (collectively, upper bars 1502). The upper bars 1502 are connected to a plurality of lower bars 1504A, 1504B, 1504C, 1504D, and 1504E (collectively referred to as lower bars 1504) by a plurality of vias such as the exemplary via 1506. As shown in FIG. 15A, the exemplary via 1506 electrically couples the upper bar 1502D to the lower bar 1504E. The features of the magnetic field generation device 1500 may be seen in the top view provide in FIG. 15B. As may be seen from these figures, the magnetic field generation device provides a coiling structure oriented horizontally to provide a horizontally aligned magnetic field, which may be used to manipulate magnetic beads that may be used to tag target bio-entities. The upper bars 1502, the coupling vias, and the lower bars 1504 may be provided as part of the metallization layers such as those shown in the fluidic control circuitry 1304 of FIG. 13 along with the electrodes 1314A-C.

Referring now to FIG. 16, an embodiment of the integrated microfluidic bio-entity manipulation system 1600 that incorporates a magnetic field generation device, like the magnetic field generation device 1500, is shown therein in cross-section. Many features of the bio-entity manipulation system 1600 are similar to those described above in connection with the system 1300 and similar features are numbered accordingly for convenience. The bio-entity manipulation system 1600 includes a magnetic field detection device 1602 that generates a horizontally-oriented magnetic field when triggered by the fluidic control circuitry 1304. The magnetic field generation device 1602 includes a plurality of uppers bars 1604A and a plurality of lower bars 1604B, which are coupled together by a plurality of vias (not depicted). The upper bars 1604A may be formed in the same layer used to create the electrodes 1314A-C. The lower bars 1604B may be formed in a layer of the metallization stack shown as part of the fluidic control circuitry 1304.

FIG. 17 is a cross-sectional diagram of a lower substrate of a microfluidic bio-entity manipulation and processing system 1700 according to some embodiments that include a magnetic field generation device. As shown, the system 1700 includes a magnetic field generation device 1702 formed over a substrate 1701. The magnetic field generation device 1702 is different from the magnetic field generation device 1315 of FIG. 13, in that is not co-planar with the electrodes 1314A-C.

Instead, as shown in FIG. 17, the magnetic field generation device 1702 is formed from the metallization stack that is used to illustrate a portion of the fluidic control circuitry 1304 and is embedded in the IMD 1312. The electrode 1314B still includes an opening to prevent the effects of the magnetic field on magnetic beads included in a droplet from being masked by an overlying conductive shield. The magnetic field generation device 1702 may be formed in another metallization layer in other embodiments.

Figure 18A:
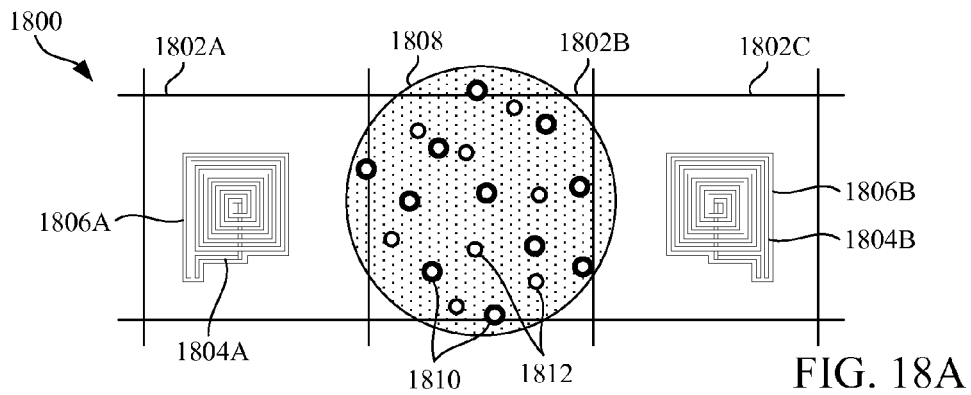
FIGS. 18A, 18B, 18C, and 18D are a series of diagrams illustrating how certain actions may be achieved using an electrowetting fluidic control system having a magnetic field generation device according to some embodiments

FIGS. 18A, 18B, 18C, and 18D are a series of top view diagrams illustrating how certain actions may be achieved using an electrowetting fluidic control system having a magnetic field generation device according to some embodiments. The features shown in FIG. 18A-D may be better in the context of FIGS. 3 and 12A-D, which illustrate several different manipulations or operations of bio-entity-containing droplets. A portion 1800 of a microfluidic grid, such as the microfluidic grid 400 of FIG. 4, is shown in top view. For example, the portion 1800 as shown may be a portion of a microfluidic channel provided in the microfluidic grid. FIG. 18A illustrates electrodes 1802A, 1802B, and 1802C; these electrodes may be similar to the electrodes 208A, 208B, and 208C illustrated in FIG. 3 and electrodes 1202A, 1202B, and 1202C of FIGS. 12A-D. In the depicted embodiment, the electrodes 1802A and 1802C each include a magnetic field generation device positioned within an opening formed in the conductive material of the respective electrodes. As illustrated, the electrode 1802A includes a magnetic field generation device 1804A situated in an opening 1806A in the conductive pad of the electrode 1802A. Similarly, the electrode 1802C includes a magnetic field generation device 1804B in an opening 1806B. As shown, the electrodes 1802A-C and the magnetic field generation devices 1804A and 1804B are coplanar. In other embodiments, the electrodes 1802A-C may be formed on a different material plane that the field generation devices 1804A and 1804B, which may be formed on different material planes from each other. The magnetic field generation devices 1804A and 1804B are depicted as being generally rectangular in shape. In other embodiments, the field generation devices 1804A and/or 1804B may be hexagonal or circular or may be configured to generate a horizontal magnetic field. Any other suitable configuration may be used within the scope of this disclosure.

As shown in FIG. 18A, a droplet 1808 is situated above the electrode 1802B. The droplet 1808 includes a plurality of bio-entities, at least some of which are tagged for identification and/or manipulations. As shown in FIG. 18A, two different kinds of magnetic beads are bound to such bio-entities in the sample droplet 1808. Magnetic beads 1810 and magnetic beads 1812 are present in the droplet 1808, with the magnetic beads 1810 bound to instances of a first target bio-entity (e.g., an antibody) and the magnetic beads 1812 bound to instances of a second, different target bio-entity (e.g., a virus) contained in the droplet 1808. The magnetic beads 1810 and 1812 are illustrated as being different from each other in size, however, the magnetic beads 1810 and 1812 may be different in size or in some other manner. For example, the magnetic beads 1810 may be 700 nanometers in diameter while the magnetic beads 1812 may be about 200 nanometers in diameter. In some embodiments, the magnetic beads 1810 and 1812 may be different in material but the same in diameter. In yet other embodiments, the magnetic beads 1810 and 1812 may differ from each other in both size and material. The differences between the magnetic beads 1810 and 1812 may permit the separation of these two groups of beads and the different bio-entities tagged thereby.

Figure 18B:
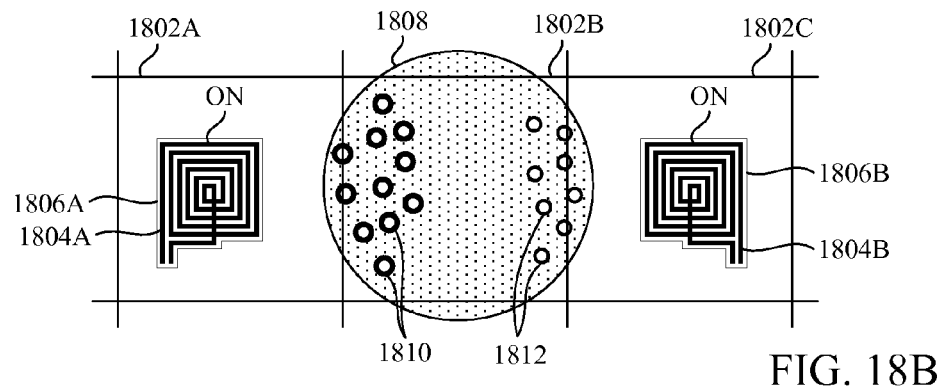

Referring now to FIG. 18B, as shown therein both of the magnetic field generation devices 1804A and 1804B are activated, producing magnetic fields. The magnetic fields produced by the magnetic field generation devices 1804A and 1804B are different in at least one aspect. For example, the magnetic field produced by the magnetic field generation device 1804A may have a greater magnitude that the magnetic field produced by the magnetic field generation device 1804B. Also, the magnetic fields may be of different durations. The duration of the magnetic field of the magnetic field generation device 1804A may be less than a duration of the magnetic field of the magnetic field generation device 1804B. In some embodiments, the durations may be proximate in time without overlapping in time. For example, the magnetic field generation device 1804B may be employed by fluidic control circuitry to produce a magnetic field for a first duration. The magnetic field may attract all of the magnetic beads 1810 and 1812 to the right side of the droplet 1808. The magnet field generation device 1804B may be deactivated and then magnetic field generation device 1804A may be activated for a short period of time. The period of time may be sufficient to attract the magnetic beads 1810, but not sufficient to attract the magnetic beads 1812 enough to move them from the right side of the droplet 1808 to the left side.

In some embodiments, a weaker magnetic field may be produced by the magnetic field generation device 1804B for a longer duration. All of the magnetic beads 1810 and 1812 may be attracted to the right side of the droplet 1808. Then, a strong magnetic field may be generated by the magnetic generation device 1804A. This stronger magnetic field may then cause a different mobility between the bio-entities tagged with the magnetic beads 1810 than that of bio-entities tagged with the magnetic beads 1812 to be exhibited. In some embodiments, a more magnetic material may be used in creating the magnetic beads 1810, such that the tagged entities and beads migrate from the right side of the droplet 1808 to the left side more quickly. In some embodiments, a smaller magnetic bead may have greater mobility within the droplet 1808 due to its size and, consequently, travel faster that a larger magnetic beads. In such ways, the magnetic beads 1810 (and associated tagged entities) may be concentrated on the left side of the droplet 1808, while the magnetic beads 1812 (and associated tagged entities) are concentrated on the right side. These differences in concentration within the droplet 1808 may be transient, such that if the electrodes 1802A and 1802C are not turned on sufficiently quickly, the tagged bio-entities and tagging magnetic beads 1810 and 1812 may diffuse throughout the droplet 1808 again.

Figure 18C:
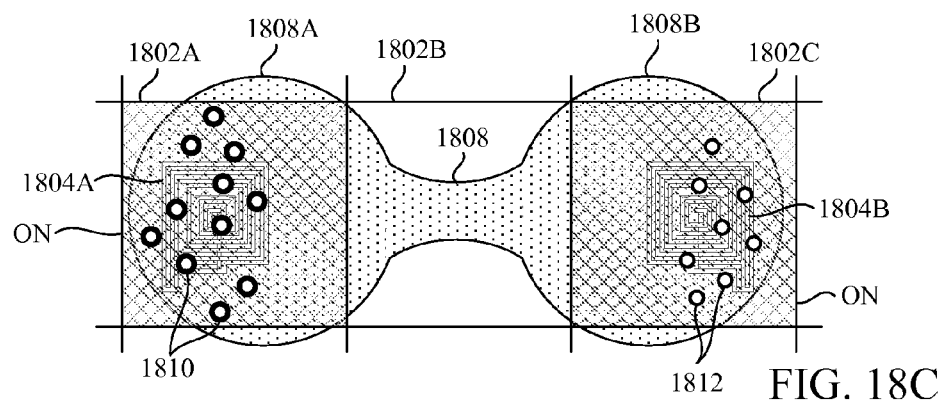
Figure 18D:
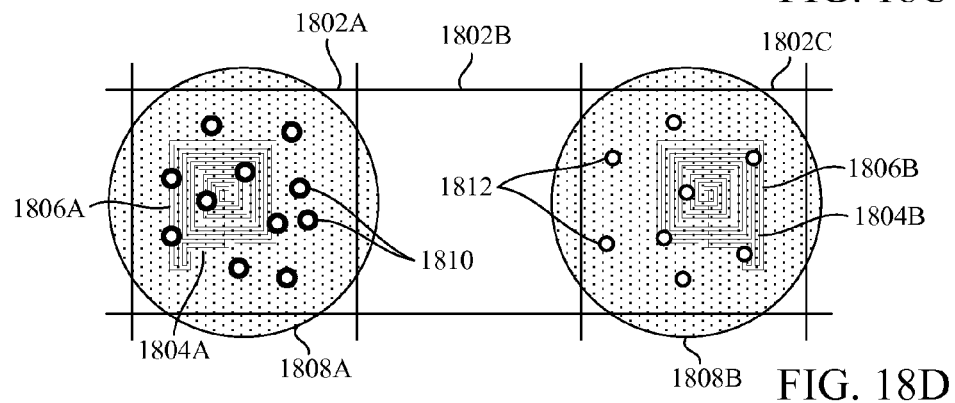

In FIG. 18C, the electrodes 1802A and 1802C are asserted by the fluidic control circuitry into an ON state, such that the droplet 1808 is split into droplet portions 1808A and 1808B as shown. Because the electrodes 1802A and 1802C are activated before the magnetic beads 1810 and 1812, with their associated tagged bio-entities, can be redisbursed throughout the droplet 1808, the droplet portion 1808A contains the magnetic beads 1810 while the droplet portion 1808B contains the magnetic beads 1812. After the splitting of the droplet 1808 into the droplet portions 1808A and 1808B, the droplet portions 1808A and 1808B may be as seen in FIG. 18D. As shown in FIG. 18D, the magnetic beads 1810 and 1812 may diffuse throughout the droplet portions 1808A and 1808B, respectively. Similarly as shown in FIG. 18D, the electrodes 1802A and 1802C are not in an activated or ON state, but are in a deactivated or OFF state. In some embodiments, in order to maintain the droplet portions 1808A and 1808B in position over the electrodes 1802A and 1802C, the electrodes may be maintained in an interstitial state. For example, rather than being completely OFF or completely ON, the electrodes 1802A and 1802C may be provided by the fluidic control circuitry with a voltage level in between an ON level and an OFF level such that it modulates the hydrophobicity of the area above the electrodes 1802A and 1802C so that the droplet portions 180A and 1808B are maintained in place.

Figure 19:
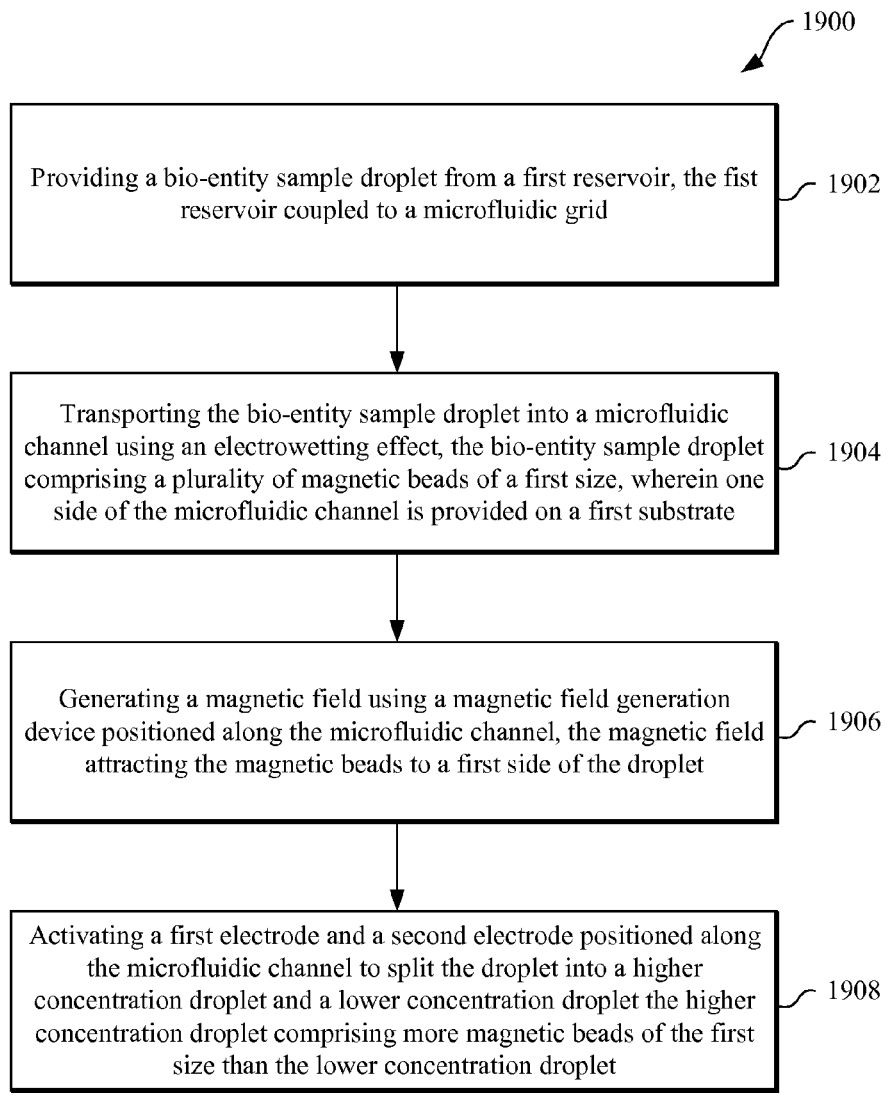
FIG. 19 is a flowchart of a method for manipulating and processing bio-entity samples with a magnetic field generation device according to some embodiments.

FIG. 19 is a flowchart of a method 1900 for manipulating and processing bio-entity samples with a magnetic field generation device according to some embodiments. As illustrated in FIG. 19, the method 1900 includes several enumerated operations. Embodiments of the method 1900 may include additional operations before, after, in between, or as part of the enumerated operations. Additionally, some embodiments of the method 1900 may not include all of the enumerated operations shown in FIG. 19. Embodiments of the method 1900 may be performed using microfluidic bio-entity manipulation and processing systems, like the systems 1300, 1600, and/or 1700 as described herein and illustrated in FIGS. 13, 16, and 17.

Embodiments of the method 1900 may begin in step 1902 in which a bio-entity sample droplet is provided from a first reservoir that is coupled to a microfluidic grid. For example, a droplet may be extracted from a reservoir such as the sample tank 410A of FIG. 4. In some embodiments, this may be done using the operation illustrated in FIG. 3 as droplet formation 300D. At step 1904, the sample droplet may be transported into a microfluidic channel using an electro-wetting effect. The bio-entity sample droplet includes a plurality of magnetic beads. One side of the microfluidic channel may be provided by a first substrate, such as the lower wafers 1301, 1601, or 1701 described herein. The microfluidic channel may be one of the vertical paths 402A-J or one of the horizontal paths 404A-L illustrated in FIG. 4. Examples of the magnetic beads may include the magnetic beads 1810 or the magnetic beads 1812 as described above.

At step 1906, a magnetic field generation device positioned along the microfluidic channel generates a magnetic field. The magnetic field attracting the magnetic beads to a first side of the droplet. For example, as illustrated in FIG. 12B, when the magnetic field generation device 1204 is activated by fluidic control circuitry, magnetic beads 1210 contained in the droplet 1208 (and being associated with specific bio-entities contained in the droplet) are pulled by the magnetic field toward the electrode 1202A.

At step 1908, a first electrode and a second electrode, which are positioned along the microfluidic channel, are activated by fluidic control circuitry to split the droplet into a higher concentration droplet and a lower concentration droplet. The higher concentration may include more magnetic beads than the lower concentration droplet.

In some embodiments of the method 1900, the plurality of magnetic beads may be provided from a second reservoir, such as the reagent tank 406A of FIG. 4. The bio-entity sample droplet and the plurality of magnetic beads may be mixed in the microfluidic grid to form a prepared sample droplet, such that the magnetic beads behind with bio-entities contained in the bio-entity sample droplet. In other embodiments, the plurality of magnetic beads may be mixed with a fluid containing bio-entities outside of the fluidic grid. The mixture is then introduced into the sample tank 410A, from which the sample droplet is obtained and introduced into the microfluidic grid.

In some embodiments, the bio-entity sample droplet further includes another plurality of magnetic beads that each have a size that is different from a size of the plurality of magnetic beads. The first plurality of magnetic beads may include magnetic beads of a first size, while the other plurality of magnetic beads comprises magnetic beads of a second size. In some embodiments, the bio-entity sample droplet includes a first plurality of magnetic beads made from a first material and another plurality of magnetic beads formed from a second, different material.

Additionally, some embodiments of the systems 1300, 1600, and 1700 that may be used to perform the method 1900 may include additional magnetic field generation devices positioned along the microfluidic channel. In such embodiments, the method 1900 may include an operation of generating another magnetic field using another magnetic field generation device positioned along the microfluidic channel. The first magnetic field and the second magnetic field may have different magnitudes and/or different durations. The first and second magnetic fields may be activated simultaneously or sequentially. Additionally, the first and second magnetic fields may overlap for a portion of their durations in some embodiments.

Figure 20:
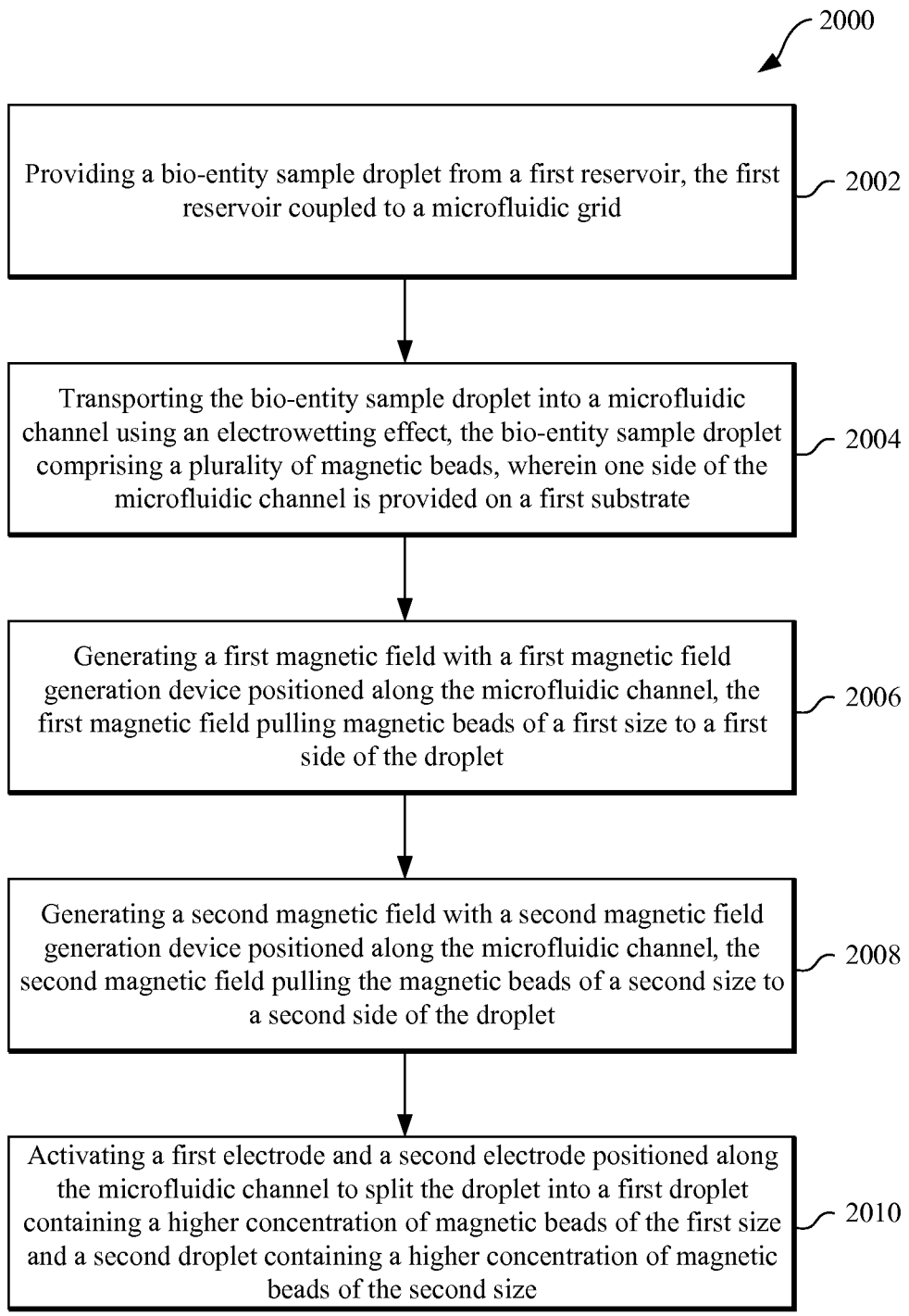
FIG. 20 is a flowchart of a method for manipulating and processing bio-entity samples with a magnetic field generation device according to some embodiments.

FIG. 20 is a flowchart of a method 2000 for manipulating and processing bio-entity samples with a magnetic field generation device according to some embodiments. Like the method 1900, the method 2000 is illustrated by a plurality of enumerated operations or steps. Additional steps may be performed before, after, in between, or as part of these enumerated steps. Further in some embodiments of the method 2000, not all of the enumerated steps may be performed. Embodiments of the method 2000 may be performed by a microfluidic bio-entity manipulation and processing systems, like the systems 1300, 1600, and/or 1700 as described herein and illustrated in FIGS. 13, 16, and 17. Further, systems used to perform the method 2000 and include a plurality of magnetic field generation devices such as the system illustrated in FIGS. 18A-D.

Embodiments of the method 2000 may begin in step 2002 in which a bio-entity sample droplet is provided from a first reservoir is coupled to a microfluidic grid. The bio-entity sample droplet may include bio-entities such as DNA, RNA, viruses, proteins, enzymes, small molecules, etc. The microfluidic grid may be similar to the microfluidic grid 400 of FIG. 4.

At step 2004, the bio-entity sample droplet is transported into a microfluidic channel using an electro-wetting effect. The bio-entity sample droplet includes a plurality of magnetic beads including magnetic beads of the first size and magnetic beads of the second size. In some embodiments of the method 2000, the plurality of magnetic beads may include magnetic beads of a first material and magnetic beads of a second material. One side of the microfluidic channel is provided over a first substrate, such as the lower wafers 1301, 1601, and/or, 1701 described herein and illustrated in FIGS. 13, 16, and 17.

At step 2006, a magnetic field is generated with a first magnetic field generation device positioned along the microfluidic channel. The first magnetic field pulls magnetic beads of a first size to a first side of the droplet. Another plurality of magnetic beads includes magnetic beads of a second size, these magnetic beads of the second size may also be pulled to the first side of the droplet by the magnetic field. At step 2008, a second magnetic field is generated with a second magnetic field generation device positioned along the microfluidic channel. The second magnetic field pulls the magnetic beads of the second size to the opposite side of the droplet. As described herein, the first magnetic field and a second magnetic field may vary in magnitude, duration, and time of assertion so as to separate the plurality of magnetic beads according to size, material, etc., between the first side of the droplet and the second side of the droplet as shown in FIG. 18B and described herein in connection with that figure and others.

At step 2010, a first electrode and a second electrode, positioned along the microfluidic channel, are activated to split the droplet into a first droplet or droplet portion containing a higher concentration of magnetic beads of the first size and a second droplet or droplet portion containing a higher concentration of magnetic beads of the second size. The combined volumes of the first droplet and the second droplet may be equal of the original sample droplet obtained from the first reservoir. In this way, droplets containing multiple different bio-entities tagged using magnetic beads may be separated according to the differences among the magnetic beads.

The embodiments described herein in embodiments within the scope of this disclosure but not explicitly described herein utilize magnetic bead tags bound to specific bio-entities in order to facilitate certain operations performed on an integrated semiconductor device in order to identify, quantify, isolate, concentrate, and separate bio-entities for research, quality control, and/or diagnostic purposes.

One of the broader embodiments is an integrated semiconductor device for manipulating and processing bio-entity samples. The device may include a microfluidic channel, the channel being coupled to fluidic control circuitry, and a photosensor array coupled to sensor control circuitry. The device may also include logic circuitry coupled to the fluidic control circuitry and the sensor control circuitry. The fluidic control circuitry, the sensor control circuitry, and the logic circuitry may be formed on a front side of a first substrate.

Another of the broader embodiments is an integrated semiconductor device for manipulating and processing genetic samples. The integrated semiconductor device may include a microfluidic channel, the microfluidic channel being coupled to fluidic control circuitry. The device may further include a photosensor array coupled to sensor control circuitry, an optical component aligned with the photosensor array to manipulate a light signal before the light signal reaches the photosensor array, and a microfluidic grid coupled to the microfluidic channel and providing for transport of genetic sample droplets by electrowetting. Additionally, the device may include logic circuitry coupled to the fluidic control circuitry and the sensor control circuitry. The fluidic control circuitry, the sensor control circuitry, and the logic circuitry are formed on first substrate.

Yet another of the broader embodiments is a method for manipulating and processing bio-entity samples with an integrated semiconductor device. The method may include steps of providing a bio-entity sample droplet from a first reservoir, the first reservoir coupled to a microfluidic grid; transporting the bio-entity sample droplet from the microfluidic grid into a microfluidic channel using an electrowetting effect, and detecting a photonic signal with a photosensor array. The bio-entity sample droplet may contact a surface treatment in the microfluidic channel, wherein one side of the microfluidic channel is provided on a first substrate. The photonic signal is enhanced by an interaction of the bio-entity sample droplet and the surface treatment, and the photosensor array is formed on the first substrate.

Another of the broader embodiments includes a device having a microfluidic channel formed between a first substrate and a second substrate, a microfluidic grid formed on the first substrate and coupled to the microfluidic channel to manipulate a droplet within the microfluidic channel, the droplet containing at least one magnetic bead, a magnetic field generation device included in the microfluidic grid, and fluidic control circuitry coupled to the magnetic device to facilitate control of the magnetic field generation device to manipulate the droplet within the microfluidic channel.

Implementations may include one or more of the following features. The device where the microfluidic grid further includes a plurality of electrodes. The device where the magnetic field generation device is formed in a material layer that includes the plurality of electrodes, and where the magnetic field generation device is positioned within an opening in one of the plurality of electrodes. The device where the fluidic control circuitry is configured to activate the magnetic field generation device independently of the one of the plurality of electrodes. The device further including a photosensor array formed in the first substrate, and where the magnetic field generation device is aligned with the photosensor array. The device where the magnetic field generation device produces a magnetic field within the magnetic field generation device that is parallel to the microfluidic channel. The device where the magnetic field generation device includes a core, the core being formed from a first material that is more magnetic than a second material from which the magnetic field generation device is formed. The integrated semiconductor device where a bottom surface of the microfluidic channel is formed on the first substrate and a top surface of the microfluidic channel is formed on a second substrate, the second substrate being coupled to the first substrate so as to provide the microfluidic channel, and where the bottom surface and the top surface of the microfluidic channel have a hydrophobic coating. The integrated semiconductor device where the first magnetic field generation device is surrounded by a first electrode of the plurality of electrodes. The integrated semiconductor device further including a second magnetic field generation device included in the microfluidic grid. The integrated semiconductor device where the fluidic control circuitry coupled to the magnetic field generation device is configured to control a duration of the magnetic field generated by the magnetic field generation device.

One general aspect includes an integrated semiconductor device of manipulating and processing bio-entity samples, the device including: a microfluidic channel formed between a first substrate and a second substrate; a microfluidic grid formed on the first substrate and coupled to the microfluidic channel to manipulate a sample droplet within the microfluidic channel, the droplet containing at least one magnetic bead, the microfluidic grid including a plurality of electrodes and a first magnetic field generation device positioned along the microfluidic channel; and fluidic control circuitry coupled to the magnetic field generation device and the plurality of electrodes to facilitate control of the magnetic field generation device to manipulate the sample droplet within the microfluidic channel. Other embodiments of this aspect include corresponding computer systems, apparatus, and computer programs recorded on one or more computer storage devices, each configured to perform the actions of the methods.

Implementations may include one or more of the following features. The integrated semiconductor device where a bottom surface of the microfluidic channel is formed over the first substrate and a top surface of the microfluidic channel is formed on a second substrate, the second substrate being coupled to the first substrate so as to provide the microfluidic channel, and where the bottom surface and the top surface of the microfluidic channel have a hydrophobic coating. The integrated semiconductor device where the first magnetic field generation device is surrounded by a first electrode of the plurality of electrodes. The integrated semiconductor device further including a second magnetic field generation device included in the microfluidic grid. The integrated semiconductor device where the fluidic control circuitry coupled to the magnetic field generation device is configured to control a duration of the magnetic field generated by the magnetic field generation device.

One general aspect includes a method for manipulating and processing bio-entity samples with an integrated semiconductor device, the method includes steps of: transporting a bio-entity-containing sample droplet into a microfluidic channel using an electrowetting effect, the sample droplet including a plurality of magnetic beads, where one side of the microfluidic channel is provided on a first substrate; generating a magnetic field using a magnetic field generation device positioned along the microfluidic channel, the magnetic field attracting the magnetic beads to a first side of the sample droplet; and activating a first electrode and a second electrode positioned along the microfluidic channel to split the sample droplet into a higher concentration droplet and a lower concentration droplet the higher concentration droplet including more magnetic beads than the lower concentration droplet. Other embodiments of this aspect include corresponding computer systems, apparatus, and computer programs recorded on one or more computer storage devices, each configured to perform the actions of the methods.

Implementations may include one or more of the following features. The method further including: providing the plurality of magnetic beads from a second reservoir coupled to a microfluidic grid by the microfluidic channel; and mixing the sample droplet and the plurality of magnetic beads in the microfluidic grid to form a prepared sample droplet, such that the magnetic beads behind with bio-entities contained in the sample droplet. The method where the sample droplet further includes another plurality of magnetic beads, and where the plurality of magnetic beads includes magnetic beads of a first size and the other plurality of magnetic beads includes magnetic beads of a second size, where the first size is different from the second size. The method where the sample droplet further includes another plurality of magnetic beads, where the plurality of magnetic beads is formed from a first material and the other plurality of magnetic beads is formed from a second material. The method where activating the first electrode and the second electrode positioned along the microfluidic channel to split the droplet splits the droplet such that the lower concentration droplet has a lower concentration of magnetic beads of a first size and a higher concentration of the magnetic beads of a second size.

Additional implementations may further include some or all of the following features. The method further including generating another magnetic field using another magnetic field generation device positioned along the microfluidic channel, and where: the magnetic field is generated for a first duration. The method may also include the other magnetic field is generated for a second duration. The method where providing a bio-entity sample droplet from a first reservoir includes providing a pre-treated bio-entity sample droplet, the pre-treated bio-entity sample droplet including the plurality of magnetic beads. The method further including generating another magnetic field using another magnetic field generation device positioned along the microfluidic channel, and where: where a magnitude of the magnetic field generated by the magnetic field generation device is greater than a magnitude of the other magnetic field generated by the other magnetic field generation device. Implementations of the described techniques may include hardware, a method or process, or computer software on a computer-accessible medium.

The preceding disclosure is submitted by way of discussion and example. It does not exhaust the full scope and spirit of the disclosure and claims. Such variations and combinations as may be apparent to one of skill in the art are considered to be within the scope and spirit of this disclosure. For instance, throughout the disclosure, DNA sequencing is presented as an example, along with pathogen identification. The scope and spirit of the disclosure extends well beyond the limited context of these examples. For example, in some embodiments, non-biological entities may be tagged with the magnetic beads and manipulated as described herein. Thus, the many features of the disclosure may be applied in non-biological, industry applications in addition to the biological applications described herein. Thus, the full extent of the disclosure is limited only by the following claims.

What is claimed is:

1. A device comprising:
    a microfluidic channel formed between a first substrate and a second substrate configured to receive a droplet therein;
    a microfluidic grid formed over the first substrate and coupled to the microfluidic channel, the microfluidic grid comprising a plurality of electrodes;
    a magnetic field generation device included in the microfluidic grid, wherein the magnetic field generation device is positioned within an opening in one of the plurality of electrodes; and
    fluidic control circuitry coupled to the magnetic field generation device to facilitate control of the magnetic field generation device to manipulate the droplet when the droplet is present and contains at least one magnetic tag within the microfluidic channel.

2. The device of claim 1, wherein the microfluidic channel is separated from the plurality of electrodes by a planar surface of a hydrophobic coating.

3. The device of claim 2, wherein the magnetic field generation device is formed in a material layer that includes the plurality of electrodes.

4. The device of claim 3, wherein the fluidic control circuitry is configured to activate the magnetic field generation device independently of the one of the plurality of electrodes.

5. The device of claim 1, further comprising a photosensor array formed in the first substrate, and wherein the magnetic field generation device is aligned with the photosensor array.

6. The device of claim 1 wherein the magnetic field generation device produces a magnetic field within the magnetic field generation device that is parallel to the microfluidic channel.

7. The device of claim 1, wherein the magnetic field generation device comprises a core, the core being formed from a first material that is more magnetic than a second material from which the magnetic field generation device is formed.

8. An integrated semiconductor device for manipulating and processing bio-entity samples, the device comprising:
    a microfluidic channel formed between a first substrate and a second substrate and configured to receive a sample droplet;
    a microfluidic grid formed over the first substrate and coupled to the microfluidic channel to manipulate the sample droplet within the microfluidic channel, the microfluidic grid comprising a plurality of electrodes and a first magnetic field generation device positioned along the microfluidic channel, wherein the first magnetic field generation device is surrounded by a first electrode of the plurality of electrodes; and
    fluidic control circuitry coupled to the magnetic field generation device and the plurality of electrodes to facilitate control of the magnetic field generation device to manipulate the sample droplet, when the sample droplet contains at least one magnetic bead within the microfluidic channel.

9. The integrated semiconductor device of claim 8, wherein a bottom surface of the microfluidic channel over formed on the first substrate and a top surface of the microfluidic channel is formed over a second substrate, the second substrate being coupled to the first substrate so as to provide the microfluidic channel, and wherein the bottom surface and the top surface of the microfluidic channel have a hydrophobic coating.

10. The integrated semiconductor device of claim 9, wherein the hydrophobic coating of the bottom surface and the hydrophobic coating of the top surface are planar throughout the microfluidic channel.

11. The integrated semiconductor device of claim 8, further comprising a second magnetic field generation device included in the microfluidic grid.

12. The integrated semiconductor device of claim 8, wherein the fluidic control circuitry coupled to the magnetic field generation device is configured to control a duration of the magnetic field generated by the magnetic field generation device.

13. A method for manipulating and processing bio-entity samples with an integrated semiconductor device, the method comprising:
transporting a bio-entity-containing sample droplet into a microfluidic channel using an electrowetting effect, the sample droplet comprising a plurality of magnetic beads, wherein one side of the microfluidic channel is provided on a first substrate;
generating a magnetic field using a magnetic field generation device positioned along the microfluidic channel and within an opening in one of a plurality of electrodes included in the microfluidic channel, the magnetic field attracting the magnetic beads to a first side of the sample droplet; and
activating a first electrode and a second electrode positioned along the microfluidic channel to split the sample droplet into a higher concentration droplet and a lower concentration droplet the higher concentration droplet comprising more magnetic beads than the lower concentration droplet.

14. The method of claim 13, further comprising:
providing the plurality of magnetic beads from a second reservoir coupled to a microfluidic grid by the microfluidic channel; and
mixing the sample droplet and the plurality of magnetic beads in the microfluidic grid to form a prepared sample droplet, such that the magnetic beads behind with bio-entities contained in the sample droplet.

15. The method of claim 13, wherein the sample droplet further comprises another plurality of magnetic beads, and wherein the plurality of magnetic beads comprises magnetic beads of a first size and the other plurality of magnetic beads comprises magnetic beads of a second size, wherein the first size is different from the second size.

16. The method of claim 13, wherein the sample droplet further comprises another plurality of magnetic beads, wherein the plurality of magnetic beads is formed from a first material and the other plurality of magnetic beads is formed from a second material.

17. The method of claim 16, wherein activating the first electrode and the second electrode positioned along the microfluidic channel to split the droplet splits the droplet such that the lower concentration droplet has a lower concentration of magnetic beads of a first size and a higher concentration of the magnetic beads of a second size.

18. The method of claim 13, further comprising generating another magnetic field using another magnetic field generation device positioned along the microfluidic channel, and wherein:
the magnetic field is generated for a first duration; and
the other magnetic field is generated for a second duration.

19. The method of claim 13, wherein providing a bio-entity sample droplet from a first reservoir comprises providing a pre-treated bio-entity sample droplet, the pre-treated bio-entity sample droplet comprising the plurality of magnetic beads.

20. The method of claim 13, further comprising generating another magnetic field using another magnetic field generation device positioned along the microfluidic channel; and
wherein a magnitude of the magnetic field generated by the magnetic field generation device is greater than a magnitude of the other magnetic field generated by the other magnetic field generation device.

\* \* \* \* \*